(12) United States Patent
Watanabe

(10) Patent No.: US 9,504,400 B2
(45) Date of Patent: Nov. 29, 2016

(54) ATRIAL FIBRILLATION ANALYZER, ATRIAL FIBRILLATION ANALYSIS SYSTEM, ATRIAL FIBRILLATION ANALYSIS METHOD, AND PROGRAM

(71) Applicant: Seiko Epson Corporation, Shinjuku-ku (JP)

(72) Inventor: Shinichiro Watanabe, Koto-ku (JP)

(73) Assignee: Seiko Epson Corporation, Tokyo (JP)

( * ) Notice: Subject to any disclaimer, the term of this patent is extended or adjusted under 35 U.S.C. 154(b) by 54 days.

(21) Appl. No.: 14/197,050

(22) Filed: Mar. 4, 2014

(65) Prior Publication Data

US 2014/0257123 A1 Sep. 11, 2014

(30) Foreign Application Priority Data

Mar. 8, 2013 (JP) ................. 2013-046648

(51) Int. Cl.
*A61B 5/0456* (2006.01)
*A61B 5/046* (2006.01)
*A61B 5/11* (2006.01)

(52) U.S. Cl.
CPC ............ *A61B 5/046* (2013.01); *A61B 5/0456* (2013.01); *A61B 5/1118* (2013.01)

(58) Field of Classification Search
CPC A61B 5/0452; A61B 5/0468; A61B 5/0456; A61B 5/046; A61B 5/1118; A61N 1/08; A61N 1/395
See application file for complete search history.

(56) References Cited

U.S. PATENT DOCUMENTS 7,727,158 B2   6/2010  Kitajima et al.
7,738,936 B1 *  6/2010  Turcott ............. A61B 5/02405
                                                    600/339
2002/0028988 A1  3/2002  Suzuki et al.
2003/0130586 A1  7/2003  Starobin et al.
(Continued)

FOREIGN PATENT DOCUMENTS

JP   1-221140 A    9/1989
JP   2001-327472 A   11/2001
(Continued)

OTHER PUBLICATIONS

Hayano, Junichiro, et al., "Spectral characteristics of ventricular response to atrial fibrillation," American Journal of Physiology—Heart and Circulatory Physiology, (1997), 273, pp. H2811-H2816.

*Primary Examiner* — William Levicky
(74) *Attorney, Agent, or Firm* — Kilpatrick Townsend & Stockton LLP

(57) ABSTRACT

An atrial fibrillation analyzer includes: an acquisition unit that acquires a waveform signal indicating a temporal change of a pulse wave or an electrocardiogram; an RR interval calculation unit that calculates a parameter corresponding to an average RR interval for each frame on the basis of a spectrum of each frame obtained by frequency analysis of the acquired waveform signal, and calculates an RR waveform signal indicating a temporal change of the parameter; a power calculation unit that calculates a temporal change of power of a predetermined frequency band in a frequency spectrum of the RR waveform signal; a variation coefficient calculation unit that calculates a variation coefficient of the average RR interval; an analysis unit that analyzes presence of atrial fibrillation on the basis of a set of the power and the variation coefficient; and a measurement unit that measures an amount of activity of a user.

8 Claims, 14 Drawing Sheets

(56) References Cited

U.S. PATENT DOCUMENTS

| | | | |
|---|---|---|---|
| 2003/0181795 A1 | 9/2003 | Suzuki et al. | |
| 2006/0161079 A1* | 7/2006 | Choi | A61B 5/1117 600/595 |
| 2006/0224072 A1* | 10/2006 | Shennib | A61B 5/6833 600/509 |
| 2008/0249423 A1* | 10/2008 | Kitajima | A61B 5/02116 600/500 |
| 2009/0076559 A1* | 3/2009 | Libbus | A61N 1/046 607/6 |
| 2009/0264783 A1* | 10/2009 | Xi | A61B 5/046 600/518 |
| 2010/0049266 A1* | 2/2010 | Ochs | A61H 31/005 607/5 |
| 2012/0095358 A1 | 4/2012 | Matsunaga et al. | |
| 2012/0165684 A1* | 6/2012 | Sholder | A61B 5/0031 600/483 |
| 2013/0060154 A1* | 3/2013 | Morita | A61B 5/0456 600/501 |

FOREIGN PATENT DOCUMENTS

| | | |
|---|---|---|
| JP | 2006-061416 A | 3/2006 |
| JP | 2007-125366 A | 5/2007 |
| JP | 2008-253579 A | 10/2008 |
| JP | 2009-089883 A | 4/2009 |
| JP | 3159276 U | 4/2010 |
| JP | 2012-081194 A | 4/2012 |
| JP | 2013-055982 A | 3/2013 |

* cited by examiner

ATRIAL FIBRILLATION ANALYZER, ATRIAL FIBRILLATION ANALYSIS SYSTEM, ATRIAL FIBRILLATION ANALYSIS METHOD, AND PROGRAM

This application claims priority to Japanese Patent Application No. 2013-046648, filed Mar. 8, 2013, the entirety of which is hereby incorporated by reference.

BACKGROUND

1. Technical Field

The present invention relates to a technique of analyzing atrial fibrillation.

2. Related Art

In the medical field related to heart disease, there is a technique of analyzing atrial fibrillation. JP-A-2009-89883 discloses a technique of measuring the RR interval obtained from an electrocardiogram of each beat and analyzing atrial fibrillation on the basis of the standard deviation and the frequency distribution. Hayano J, Yamasaki F, Sakata S, Okada A, Mukai S, Fujinami T "Spectral characteristics of ventricular response to atrial fibrillation" Am. J. Physiol. 1997; 273: H2811-H2816 discloses that the RR interval during atrial fibrillation is irregular, a 1/fβ component is present when the frequency analysis of cardiac beats of atrial fibrillation is performed, and a white noise pattern appears due to this variation.

In JP-A-2009-89883 and Hayano J, Yamasaki F, Sakata S, Okada A, Mukai S, Fujinami T "Spectral characteristics of ventricular response to atrial fibrillation" Am. J. Physiol. 1997; 273: H2811-H2816, it is necessary to measure the RR interval of each beat accurately for the exact analysis of atrial fibrillation. The RR interval can be measured not only from the electrocardiogram waveform signal obtained by measuring an electrocardiogram but also from the pulse wave signal obtained by measuring a pulse wave.

However, in the case of measuring the pulse wave, the subject can move freely during the measurement in many cases. Accordingly, the influence of body movement noise is likely to be included in the pulse wave signal. Also in the case of measuring the electrocardiogram, the influence of body movement noise is likely to be included in the waveform signal of the electrocardiogram although there is a difference compared with the case where the pulse wave is measured. When there is such influence of body movement noise, it is very difficult to measure the RR interval of each beat accurately.

For this reason, when the measurement of exact RR interval of each beat is a precondition as in JP-A-2009-89883 and Hayano J, Yamasaki F, Sakata S, Okada A, Mukai S, Fujinami T "Spectral characteristics of ventricular response to atrial fibrillation" Am. J. Physiol. 1997; 273: H2811-H2816, it has not been possible to analyze atrial fibrillation using a signal in which the influence of body movement noise is included. In addition, although it is known that the onset of atrial fibrillation may also be influenced by the amount of activity of the patient, the relationship between the amount of activity and the atrial fibrillation has not been fully examined since there are individual differences.

SUMMARY

An advantage of some aspects of the invention is to analyze atrial fibrillation from a signal from which an RR interval can be measured, such as a pulse wave signal and a waveform signal of an electrocardiogram, even if the influence of body movement noise is included in the signal. Another advantage of some aspects of the invention is to compare the atrial fibrillation analyzed in this manner with the amount of activity of the patient.

An aspect of the invention is directed to an atrial fibrillation analyzer including: an acquisition unit that acquires a detected waveform signal indicating a temporal change of a detection result of a pulse wave or an electrocardiogram; a waveform storage unit that stores the acquired detected waveform signal; an RR interval calculation unit that calculates, on the basis of a frequency spectrum of each unit time obtained by frequency analysis of the acquired detected waveform signal, a parameter corresponding to an average RR interval every unit time; a power calculation unit that calculates power of a frequency band determined in advance in a frequency spectrum of an RR waveform signal indicating a temporal change of the average RR interval calculated by the RR interval calculation unit; a variation coefficient calculation unit that calculates a variation coefficient of the average RR interval in the RR waveform signal; an analysis unit that analyzes presence of atrial fibrillation at each time on the basis of a set of the power and the variation coefficient; a measurement unit that measures an amount of activity of a user; and a first storage unit that stores the amount of activity measured by the measurement unit and a time when the amount of activity is measured so as to match each other.

According to this atrial fibrillation analyzer, even if the influence of body movement noise is included in a signal from which an average RR interval can be measured, such as a pulse wave signal and a waveform signal of an electrocardiogram, atrial fibrillation can be analyzed from the signal. As a result, it is possible to compare the atrial fibrillation with the amount of activity of the user.

In a preferred aspect of the invention, the atrial fibrillation analyzer described above may further include a second storage unit that stores action data, which indicates an action of the user, at each time of the action.

According to this atrial fibrillation analyzer, it is possible to compare the onset time of atrial fibrillation with the time of the action of the user.

In a preferred aspect of the invention, the atrial fibrillation analyzer described above may further include: a range storage unit that stores range information indicating a range where the amount of activity of the user is changeable; and a conversion unit that converts the amount of activity measured by the measurement unit into an amount of load, which indicates a load for the user, on the basis of the range information stored in the range storage unit.

According to this atrial fibrillation analyzer, it is possible to reflect the individual differences of the user when comparing the atrial fibrillation with the amount of activity of the user.

In a preferred aspect of the invention, the atrial fibrillation analyzer described above may further include a third storage unit that stores subjective symptom data, which indicates the atrial fibrillation that the user is aware of, each time the user is aware of the atrial fibrillation.

According to this atrial fibrillation analyzer, it is possible to compare the onset time of atrial fibrillation with the time when the user is aware of the symptom.

In a preferred aspect of the invention, the atrial fibrillation analyzer described above may further include: an operation unit that is operated by the user; and a notification unit that, when the amount of activity measured by the measurement unit exceeds a predetermined threshold value, notifies the user that the amount of activity has exceeded the threshold value so that the user operates the operation unit. The second storage unit may store the action data when the operation unit is operated by the user.

According to this atrial fibrillation analyzer, it is possible to prompt the user to perform an operation for storing action data according to the amount of activity of the user.

In a preferred aspect of the invention, the atrial fibrillation analyzer described above may further include an evaluation unit that evaluates the amount of activity measured by the measurement unit during onset of the atrial fibrillation analyzed to be present by the analysis unit.

According to this atrial fibrillation analyzer, it is possible to evaluate the amount of activity of the user according to the presence of atrial fibrillation.

Another aspect of the invention is directed to an atrial fibrillation analysis system including: the atrial fibrillation analyzer described above; a processing device that acquires the amount of activity measured by the measurement unit and processes data indicating the amount of activity on the basis of an analysis result of the analysis unit; and a presentation device that presents the data processed by the processing device.

According to this atrial fibrillation analysis system, even if the influence of body movement noise is included in a signal from which an average RR interval can be measured, such as a pulse wave signal and a waveform signal of an electrocardiogram, atrial fibrillation can be analyzed from the signal. As a result, it is possible to compare the atrial fibrillation with the amount of activity of the user.

Still another aspect of the invention is directed to an atrial fibrillation analysis method including: acquiring a detected waveform signal indicating a temporal change of a detection result of a pulse wave or an electrocardiogram; storing the acquired detected waveform signal; calculating, on the basis of a frequency spectrum of each unit time obtained by frequency analysis of the acquired detected waveform signal, a parameter corresponding to an average RR interval every unit time; calculating power of a frequency band determined in advance in a frequency spectrum of an RR waveform signal indicating a temporal change of the calculated average RR interval; calculating a variation coefficient of the average RR interval in the RR waveform signal; analyzing presence of atrial fibrillation at each time on the basis of a set of the power and the variation coefficient; measuring an amount of activity of a user; and storing the measured amount of activity and a time when the amount of activity is measured so as to match each other.

According to this atrial fibrillation analysis method, even if the influence of body movement noise is included in a signal from which an average RR interval can be measured, such as a pulse wave signal and a waveform signal of an electrocardiogram, atrial fibrillation can be analyzed from the signal. As a result, it is possible to compare the atrial fibrillation with the amount of activity of the user.

Yet another aspect of the invention is directed to a program causing a computer to execute: acquiring a detected waveform signal indicating a temporal change of a detection result of a pulse wave or an electrocardiogram; storing the acquired detected waveform signal; calculating, on the basis of a frequency spectrum of each unit time obtained by frequency analysis of the acquired detected waveform signal, a parameter corresponding to an average RR interval every unit time; calculating power of a frequency band determined in advance in a frequency spectrum of an RR waveform signal indicating a temporal change of the calculated average RR interval; calculating a variation coefficient of the average RR interval in the RR waveform signal; analyzing presence of atrial fibrillation at each time on the basis of a set of the power and the variation coefficient; measuring an amount of activity of a user; and storing the measured amount of activity and a time when the amount of activity is measured so as to match each other.

According to this program, even if the influence of body movement noise is included in a signal from which an average RR interval can be measured, such as a pulse wave signal and a waveform signal of an electrocardiogram, atrial fibrillation can be analyzed from the signal. As a result, it is possible to compare the atrial fibrillation with the amount of activity of the user.

BRIEF DESCRIPTION OF THE DRAWINGS

The invention will be described with reference to the accompanying drawings, wherein like numbers reference like elements.

DESCRIPTION OF EXEMPLARY EMBODIMENTS

Embodiments

Outline

When analyzing the atrial fibrillation from an electrocardiogram in the related art, an RR interval (hereinafter, referred to as an "electrocardiogram RR interval") of each beat has been used. In contrast, in the present embodiment, atrial fibrillation is analyzed from the pulse wave. When using the pulse wave, it may be difficult to specify the RR interval of each beat accurately unlike the electrocardiogram. For this reason, in the present embodiment, a value indicating the average of the RR interval (hereinafter, referred to as an "average pulse wave RR interval") within a certain unit time (hereinafter, referred to as a frame) is used. Here, an atrial fibrillation analysis method using the electrocardiogram RR interval will be described first, and then problems when using the average pulse wave RR interval will be described. Finally, the outline of the analysis method according to the present embodiment will be described.

Figure 10A:
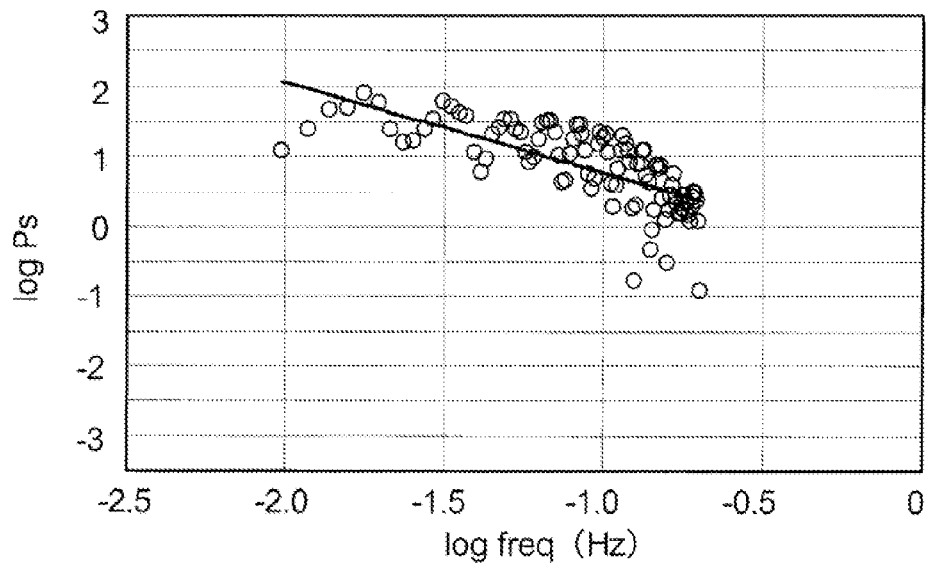
FIGS. 10A and 10B are diagrams illustrating an atrial fibrillation analysis method using the electrocardiogram RR interval.
Figure 10B:
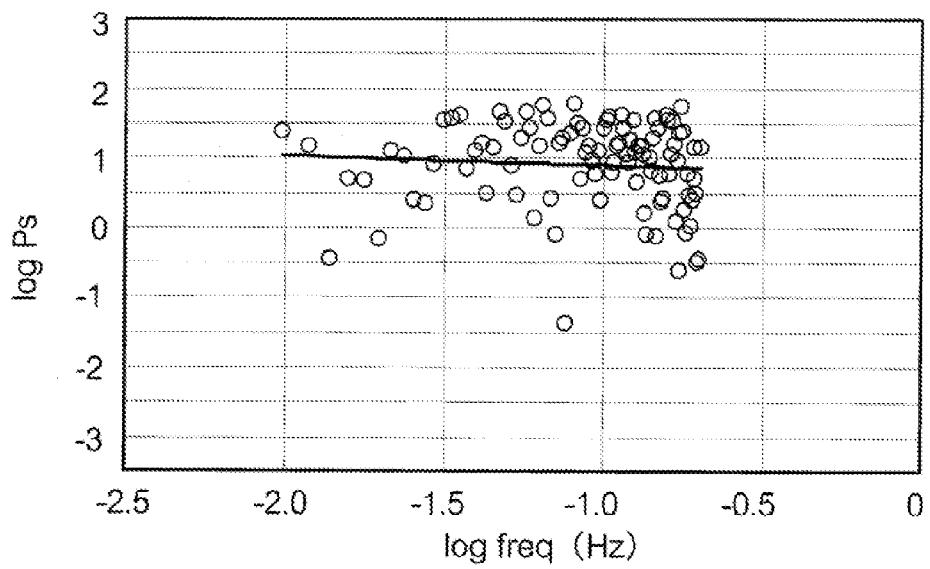

FIGS. 10A and 10B are diagrams illustrating an atrial fibrillation analysis method using the electrocardiogram RR interval. FIGS. 10A and 10B are graphs expressed by performing frequency analysis in a band of 0.01 Hz to 0.2 Hz of one frame (480 seconds) for a waveform signal indicating a change in the electrocardiogram RR interval and performing logarithmic conversion of a peak frequency and power. The power is the spectral density. FIG. 10A shows a case of using the electrocardiogram RR interval when atrial fibrillation has not developed, and FIG. 10B shows a case of using the electrocardiogram RR interval when atrial fibrillation has developed. The straight line in the diagram shows a linear regression line obtained from the plotted data. The result when the correlation coefficient $\gamma$ and the inclination $\beta$ of the linear regression line are calculated from these graphs is as follows.

In the case where atrial fibrillation has not developed as shown in FIG. 10A, $\gamma=-0.72$ and $\beta=-1.29$. In addition, in the case where atrial fibrillation has developed as shown in FIG. 10B, $\gamma=-0.07$ and $\beta=-0.13$. Thus, when atrial fibrillation has developed, it can be seen that correlation is lost and a white noise pattern appears and that the inclination $\beta$ is close to "0". Accordingly, when using the electrocardiogram RR interval, the presence of atrial fibrillation can be determined from the correlation coefficient $\gamma$ and the inclination $\beta$ of the linear regression line in a plot of peak frequency and power.

Figure 11A:
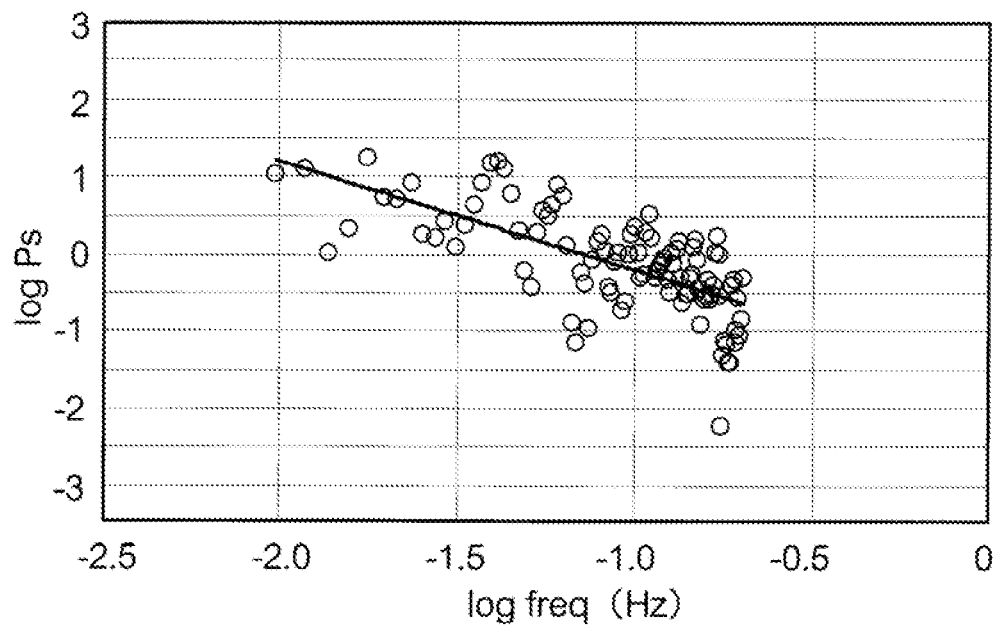
FIGS. 11A and 11B are diagrams illustrating the problems of the atrial fibrillation analysis method using the average pulse wave RR interval.
Figure 11B:
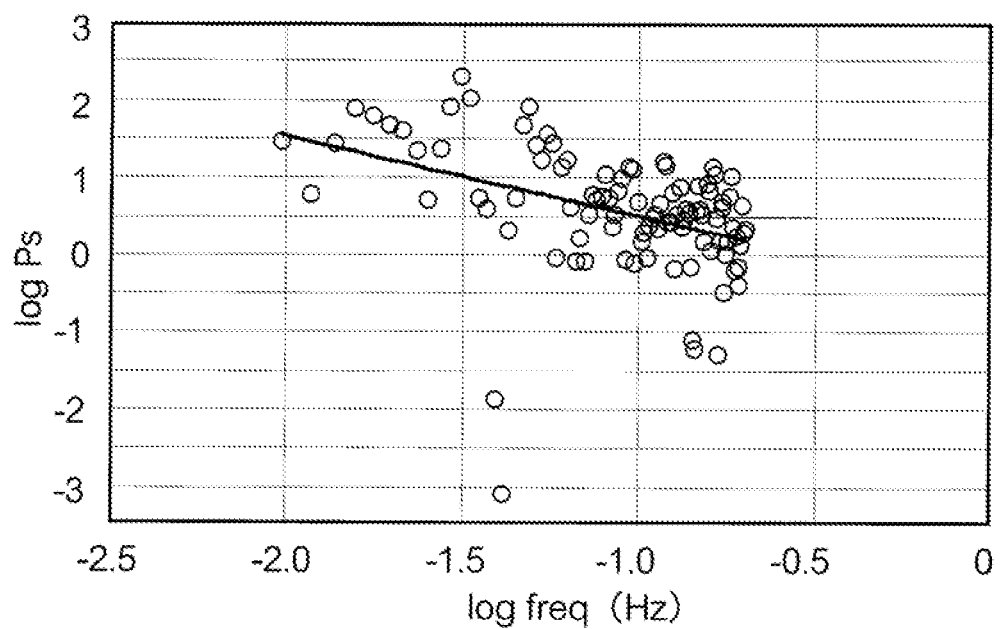

FIGS. 11A and 11B are diagrams illustrating the problems of the atrial fibrillation analysis method using the average pulse wave RR interval. FIGS. 11A and 11B are graphs expressed by performing frequency analysis in a band of 0.01 Hz to 0.2 Hz of one frame (480 seconds) for a waveform signal indicating a change in the average pulse wave RR interval and performing logarithmic conversion of a peak frequency and power. FIG. 11A shows an example where atrial fibrillation has not developed, and FIG. 11B shows an example where atrial fibrillation has developed. The straight line in the diagram shows a primary regression line obtained from the plotted data.

In the case where atrial fibrillation has not developed as shown in FIG. 11A, $\gamma=-0.68$ and $\beta=-1.40$. In addition, in the case where atrial fibrillation has developed as shown in FIG. 11B, $\gamma=-0.41$ and $\beta=-1.02$. Thus, when using the average pulse wave RR interval, there is no significant difference of $\gamma$ and $\beta$ due to the presence of atrial fibrillation, as shown in FIGS. 11A and 11B. Accordingly, determination of the presence of atrial fibrillation is difficult if the same method as when using the electrocardiogram RR interval is used.

Here, if FIGS. 10A and 10B are compared again, it can be seen that the power is increased on the high frequency band side when atrial fibrillation has developed. For example, in FIGS. 10A and 10B, when comparing the power for a frequency band around 0.2 Hz, power when atrial fibrillation has not developed is "1.59" and power when atrial fibrillation has developed is "4.97". When atrial fibrillation has developed, the power in this frequency band is increased several times and accordingly a significant difference can be seen, compared with that when atrial fibrillation has not developed.

This increase in power is also observed when using the average pulse wave RR interval. In FIGS. 11A and 11B, when comparing the power for a frequency band around 0.2 Hz, power when atrial fibrillation has not developed is "0.05" and power when atrial fibrillation has developed is "0.30". Thus, even if the average pulse wave RR interval is used, when atrial fibrillation has developed, the power in this frequency band is increased several times and accordingly a significant difference can be seen, compared with that when atrial fibrillation has not developed. In the present embodiment, the presence of atrial fibrillation is determined using the increase in power as an indicator.

In the present embodiment, a variation coefficient is used as another indicator of the presence of atrial fibrillation. The variation coefficient is a parameter indicating the degree of a variation with respect to the average of the average pulse wave RR interval. When atrial fibrillation develops, irregularity of the RR interval occurs. That is, the time interval of each beat becomes irregular. The same is true for the average pulse wave RR interval, and an irregular state (average variation) can be an indicator of atrial fibrillation. In the present embodiment, the presence of atrial fibrillation is determined using the power and the variation coefficient as indicators. Hereinafter, the device configuration and operation in the present embodiment will be described in detail.

Configuration of an Atrial Fibrillation Analysis System 9

Figure 1:
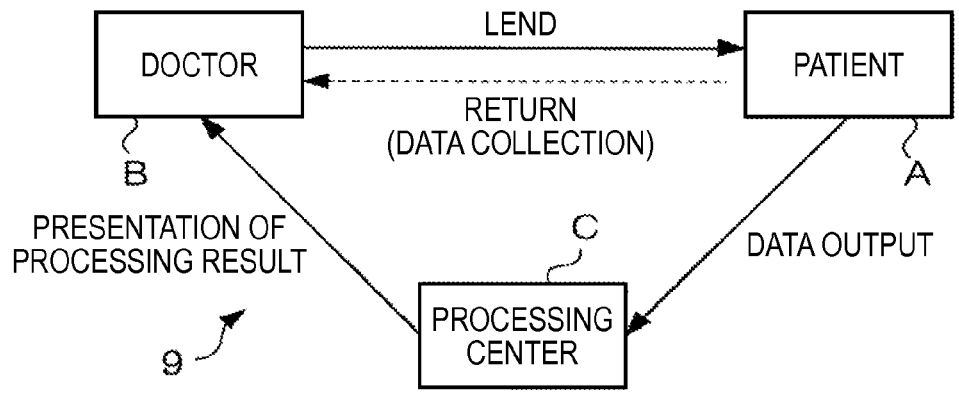
FIG. 1 is a diagram for explaining the configuration of an atrial fibrillation analysis system according to an embodiment.

FIG. 1 is a diagram for explaining the configuration of an atrial fibrillation analysis system 9 according to an embodiment. A patient A is a person who sees a doctor to examine atrial fibrillation. A doctor B is a doctor in charge of the patient A, and lends a pulse wave measuring device 1 for the diagnosis of atrial fibrillation to the patient A. The patient A is a user who uses the pulse wave measuring device 1 with the lent pulse wave measuring device 1 mounted thereon. A processing center C is a facility that receives the output of data obtained from the pulse wave measuring device 1 mounted on the patient A and processes the data according to the determined procedure. The doctor B receives the presentation of the data processed in the processing center C and makes a diagnosis regarding atrial fibrillation of the patient A.

In the embodiment described below, the pulse wave measuring device 1 may have the processing function of the processing center C.

Configuration of the Pulse Wave Measuring Device 1

Figure 2A:
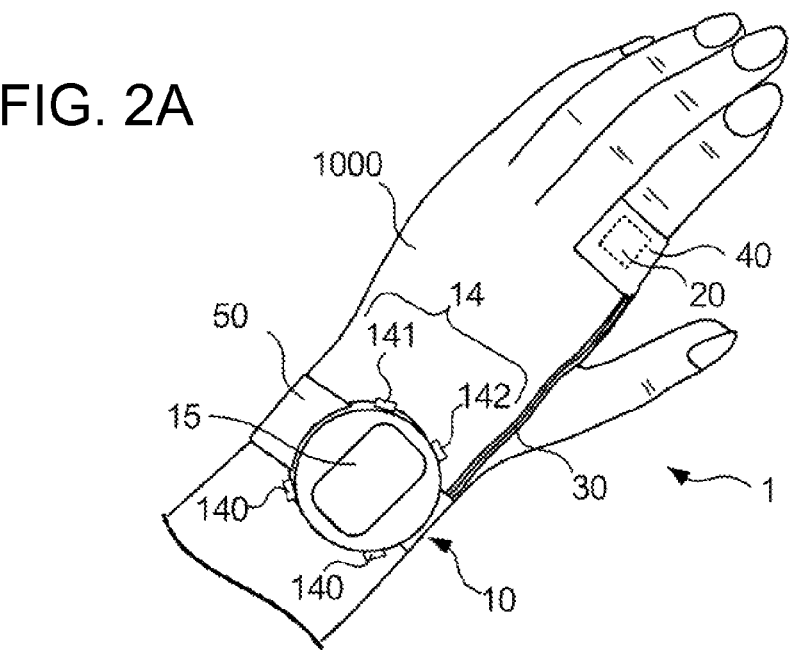
FIGS. 2A and 2B are diagrams illustrating the appearance of a pulse wave measuring device according to the embodiment.
Figure 2B:
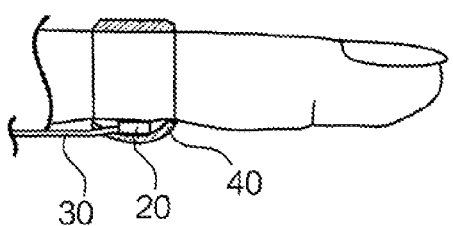

FIGS. 2A and 2B are diagrams illustrating the appearance of the pulse wave measuring device 1 according to the embodiment. As shown in FIG. 2A, the pulse wave measuring device 1 according to the embodiment of the invention includes a device body 10 mounted in the manner of a wristwatch on a wrist portion (arm) in a hand 1000 of a target person, who is a user, and a pulse wave detector 20 that is mounted on a detection portion and detects a pulse wave. The device body 10 and the pulse wave detector 20 are connected to each other through a cable 30. Through the cable 30, a pulse wave signal (hereinafter, referred to as a detected waveform signal L) output from the pulse wave detector 20 is supplied to the device body 10 and electric power from the device body 10 is supplied to the pulse wave detector 20.

A wristband 50 is attached to the device body 10. The device body 10 is mounted on the arm by wrapping the wristband 50 around the arm of the user. An operation unit 14 and a display unit 15 are provided in the device body 10. The operation unit 14 includes operators, such as button switches used when a user inputs an instruction of function selection or the like to the pulse wave measuring device 1, and receives an operation of the user through these operators. The operation unit 14 includes two button switches on each of the left and right side surfaces of the device body 10. Among these buttons, when the device body 10 is mounted on the wrist portion of the user using the wristband 50, a button switch provided in the little finger side is an action button 141 and a button switch provided on the thumb side is a subjective symptom button 142. In addition, among the buttons, two buttons provided on the elbow (not shown) side of the user are operation buttons 140 having other functions. A touch sensor or the like provided on the display unit 15 may be included in the operation unit 14. The display unit 15 is a display device, such as a liquid crystal display or an organic EL display.

As shown in FIG. 2B, in this example, a detection portion on which the pulse wave detector 20 is mounted is assumed to be a part of a region from the base of the index finger to the second finger joint in the hand 1000. However, the detection portion on which the pulse wave detector 20 is mounted may be any portion as long as it is a portion in which a pulse wave can be detected. The pulse wave detector 20 is mounted on the detection portion by being fixed by a fixing band 40. In this case, the fixing band 40 is in a state covering the pulse wave detector 20, and a light receiving unit of the pulse wave detector 20 is shielded so that light from the outside of the fixing band 40 does not reach the light receiving unit.

The pulse wave detector 20 detects a pulse wave as follows, and outputs the detected waveform signal L indicating the detection result. The pulse wave detector 20 includes a light emitting unit (for example, a green light emitting diode (LED)) and a light receiving unit. The pulse wave detector 20 emits light corresponding to the electric power, which is supplied from the device body 10 through the cable 30, from the light emitting unit. The pulse wave detector 20 receives light reflected by hemoglobin in the capillaries, of the light from the light emitting unit, through the light receiving unit, and supplies a signal corresponding to the light receiving level to the device body 10 through the cable 30 as the detected waveform signal L.

Figure 3:
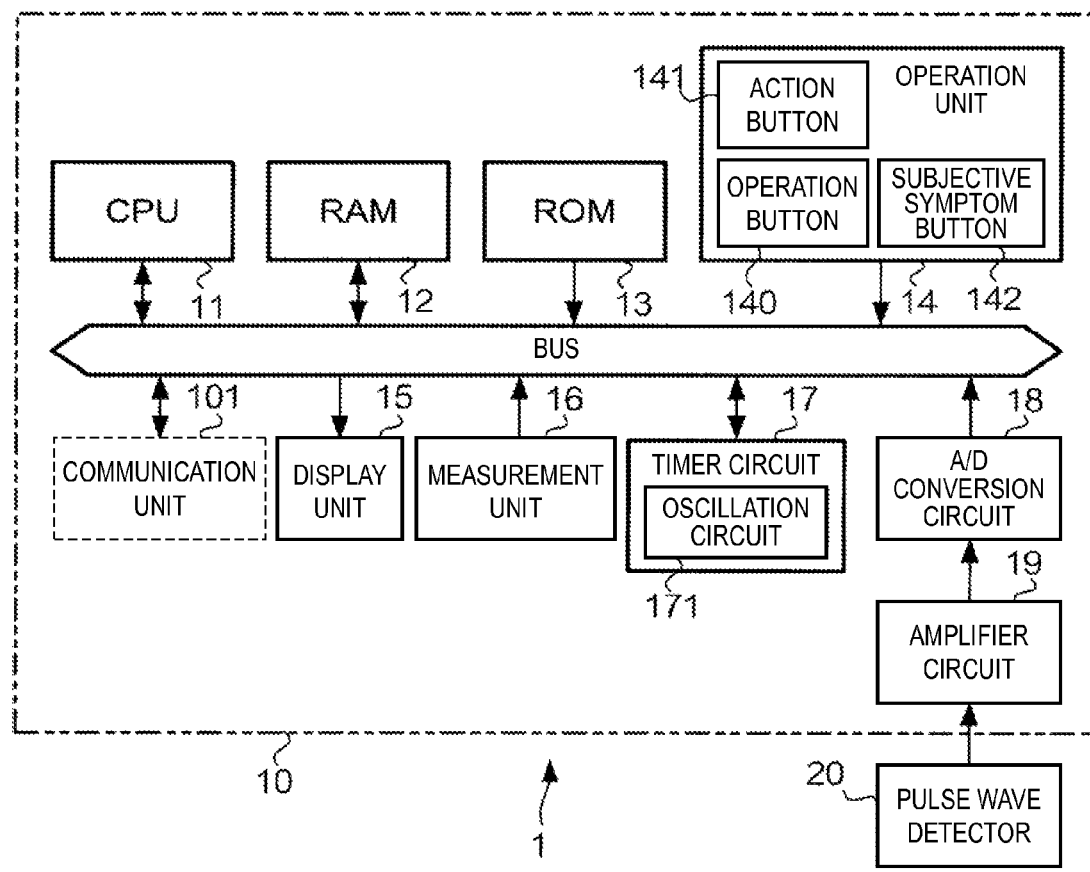
FIG. 3 is a diagram illustrating the configuration of the pulse wave measuring device according to the embodiment.

FIG. 3 is a diagram illustrating the configuration of the pulse wave measuring device 1 according to the embodiment. The pulse wave measuring device 1 includes: the device body 10 including a central processing unit (CPU) 11, a random access memory (RAM) 12, a read only memory (ROM) 13, the operation unit 14, the display unit 15, a measurement unit 16, a timer circuit 17, an A/D conversion circuit 18, and an amplifier circuit 19; and the pulse wave detector 20. The respective components excluding the amplifier circuit 19 and the pulse wave detector 20 are connected to each other through a bus.

The CPU 11 performs control of each component, data transmission, and the like according to a control program stored in the ROM 13. The RAM 12 temporarily stores biological information, such as the detected waveform signal L, and various kinds of data generated during the execution of the control program in the CPU 11. The CPU 11 realizes an atrial fibrillation analysis function by executing the control program, so that the pulse wave measuring device 1 functions as an atrial fibrillation analyzer. In addition, the CPU 11 may realize various functions other than the atrial fibrillation analysis function by executing the control program. It is preferable to realize these functions, for example, by causing the user to operate the operation unit 14.

As described above, the operation unit 14 includes button switches for inputting an instruction of the user to the pulse wave measuring device 1. When the operation unit 14 is operated by the user, the operation unit 14 outputs an operation signal indicating the operation content to the CPU 11. Among the button switches provided in the operation unit 14, the action button 141 is an operator pressed when the user performs a predetermined action. In addition, the subjective symptom button 142 is an operator pressed when the user acquires the subjective symptoms of atrial fibrillation.

The display unit 15 includes a display device, such as a liquid crystal display or an organic EL display, as described above, and the display content is controlled by the CPU 11. This display content is various images indicating time display, various menu screens, a pulse wave measurement result, and an atrial fibrillation analysis result, for example.

The measurement unit 16 is a sensor that is mounted inside the housing of the device body 10 and that detects body movement, which is an operation of the mounting portion (in the present embodiment, a wrist), and outputs a signal corresponding to the detection result. Since this signal indicates the degree of the body movement, the amount of activity of the user is calculated on the basis of the signal. That is, the measurement unit 16 is equivalent to a measurement unit that measures the amount of activity of the user. In addition, the amount of activity is an amount indicating the degree of activity of the body. For example, the amount of activity is calories consumed by the activity of the body.

Specifically, the measurement unit 16 includes a capacitive acceleration sensor, a piezoresistive acceleration sensor, or the like, and detects the acceleration in three axial directions. In addition, the measurement unit 16 calculates the absolute value of the acceleration of the above-described mounting portion or the amount of activity of the user on the basis of the detected acceleration in the three axial directions, for example, and outputs the absolute value or the amount of activity to the CPU 11.

The timer circuit 17 includes an oscillation circuit 171. The oscillation circuit 171 supplies a clock signal as a basis for control to the CPU 11. The timer circuit 17 measures the time under the control of the CPU 11.

When the action button 141 or the subjective symptom button 142 is pressed, the CPU 11 stores the timing in the RAM 12 with reference to the time measured by the timer circuit 17.

The amplifier circuit 19 amplifies the detected waveform signal L supplied from the pulse wave detector 20 through the cable 30. The gain at the time of amplification is set by the control of the CPU 11.

The A/D conversion circuit 18 converts the detected waveform signal L, which is an analog signal, amplified by the amplifier circuit 19 into a digital signal. In this example, the sampling frequency is 100 Hz, and is a sufficiently high frequency compared with an RR interval obtained from the pulse wave. In addition, in this example, quantization is performed in 10 bits. In addition, for the sampling frequency and the quantization bit, different values may be determined according to the required accuracy.

Subsequently, the functional configuration (atrial fibrillation analysis function and storage function) of the atrial fibrillation analyzer realized by the CPU 11 will be described.

Functional Configuration

Figure 4:
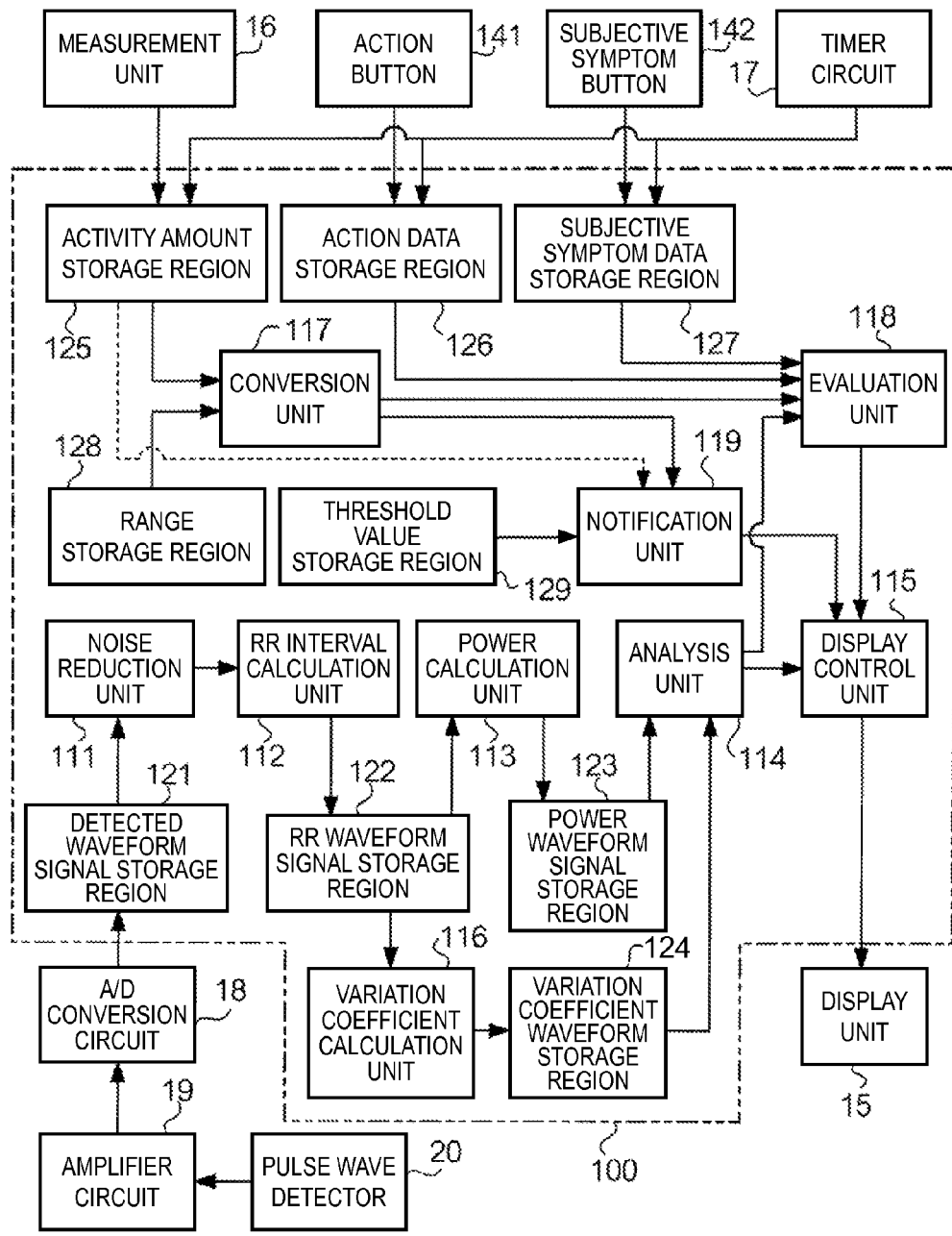
FIG. 4 is a diagram illustrating the functional configuration of an atrial fibrillation analyzer according to the embodiment.

FIG. 4 is a diagram illustrating the functional configuration of an atrial fibrillation analyzer 100 according to the embodiment. The atrial fibrillation analyzer 100 includes a noise reduction unit 111, an RR interval calculation unit 112, a power calculation unit 113, an analysis unit 114, a display control unit 115, a variation coefficient calculation unit 116, a conversion unit 117, an evaluation unit 118, and a notification unit 119, and is realized by each functional configuration of a detected waveform signal storage region 121, an RR waveform signal storage region 122, a power waveform signal storage region 123, a variation coefficient waveform storage region 124, an activity amount storage region 125, an action data storage region 126, a subjective symptom data storage region 127, a range storage region 128, and a threshold value storage region 129 that are storage regions of various kinds of data.

The detected waveform signal storage region 121 is a region provided on the RAM 12 in which the detected waveform signal L converted into a digital signal by the A/D conversion circuit 18 is stored.

The noise reduction unit 111 performs a filtering process for reducing body movement noise components other than the frequency band, which corresponds to the RR interval, from the detected waveform signal L stored in the detected waveform signal storage region 121 and outputs the result. Examples of the filtering process include a process of a high pass filter, a process of a band pass filter, and a process of an adaptive filter. The detected waveform signal L from which body movement noise components have been reduced by the noise reduction unit 111 may be temporarily stored in the RAM 12. The noise reduction unit 111 and the detected waveform signal storage region 121 function as an acquisition unit that acquires the detected waveform signal L used in the frequency analysis of the RR interval calculation unit 112.

In addition, since the body movement noise components are reduced by this filtering process, the influence is reduced from the detected waveform signal L. However, it is not possible to measure the exact RR interval so as to be able to analyze atrial fibrillation accurately in the technique (JP-A-2009-89883 and Hayano J, Yamasaki F, Sakata S, Okada A, Mukai S, Fujinami T "Spectral characteristics of ventricular response to atrial fibrillation" Am. J. Physiol. 1997; 273: H2811-H2816) presented as the related art.

For the detected waveform signal L from which body movement noise components have been reduced by the noise reduction unit 111, the RR interval calculation unit 112 cuts a frame in each sampling, and calculates a frequency spectrum by frequency analysis in a short time (STFT (Short-Time Fourier Transform) analysis). Then, the RR interval calculation unit 112 calculates a parameter corresponding to the RR interval for each frame on the basis of the calculated frequency spectrum, and stores an RR waveform signal FRR, which indicates a temporal change of the parameter, in the RR waveform signal storage region 122 provided on the RAM 12. In addition, the RR waveform signal FRR is a set of data indicating a temporal change of this parameter.

In this example, the calculated parameter is a value (average pulse wave RR interval) indicating the average of the RR interval in a frame. For example, the calculated parameter is a frequency at which a maximum peak of the frequency spectrum is obtained. Accordingly, the RR waveform signal FRR indicates a temporal change of the average pulse wave RR interval. By the process of the RR interval calculation unit 112, the influence of the body movement noise included in the RR waveform signal FRR can be greatly reduced even if the body movement noise is not completely removed by the noise reduction unit 111.

Figure 5:
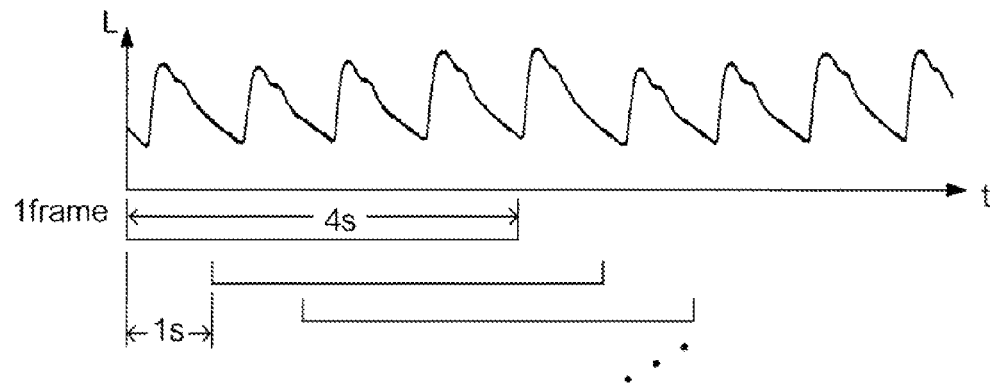
FIG. 5 is a diagram illustrating a frame when performing frequency analysis of a detected waveform signal.

FIG. 5 is a diagram illustrating a frame when performing frequency analysis of the detected waveform signal L. The waveform shown in FIG. 5 is an example of the waveform of the detected waveform signal L. As shown in FIG. 5, the period of each frame is 4 seconds in this example, and frequency analysis is performed after sampling every second. That is, each frame is set so as to be shifted by 1 second, and overlaps the next frame for 3 seconds. Since the sampling timing and a frame are set as described above, the average pulse wave RR interval is an average value of 4 seconds of the RR interval, and the RR waveform signal FRR indicates a change in the average pulse wave RR interval every second.

Figure 6:
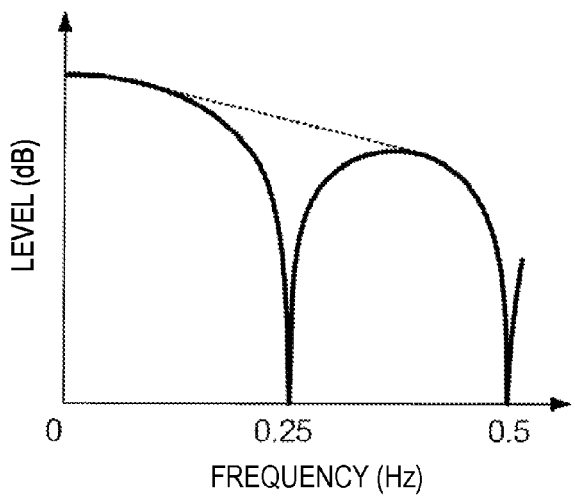
FIG. 6 is a diagram illustrating the frequency characteristics in an RR interval calculation unit.

FIG. 6 is a diagram illustrating the frequency characteristics in the RR interval calculation unit 112. Performing frequency analysis with the frame set as described above in the RR interval calculation unit 112 is equivalent to "frequency characteristics are superimposed in the movement averaging process". In the frequency characteristics shown in FIG. 6, valleys occur at the frequency of 0.25 Hz equivalent to 4 seconds of the time of the frame and frequencies of integral multiples of 0.25 Hz. In addition, as an overall trend when connecting the peaks of the mountains, the level becomes lower as the frequency becomes higher. That is, the frequency characteristics shown in FIG. 6 are frequency characteristics having a negative inclination. The inclination becomes steeper as the period of a frame becomes longer. On the other hand, as the period of a frame becomes shorter, the inclination becomes closer to "0", but the amount of body movement noise components in the detected waveform signal L is increased. Therefore, it is preferable to set the frame period to 1 second or more and 5 seconds or less. More preferably, the frame period is set to 2 seconds or more and 4 seconds or less.

The power calculation unit 113 performs frequency analysis in a short time (STFT analysis) for the RR waveform signal FRR stored in the RR waveform signal storage region 122, and calculates power (hereinafter, referred to as band power) of a part of a frequency band (hereinafter, referred to as a calculation frequency band) on the basis of the obtained frequency spectrum. The power calculation unit 113 stores a power waveform signal Pa, which indicates a temporal change of the calculated band power, in the power waveform signal storage region 123 provided on the RAM 12. In addition, the power waveform signal Pa is a set of data indicating a temporal change of band power.

Figure 7:
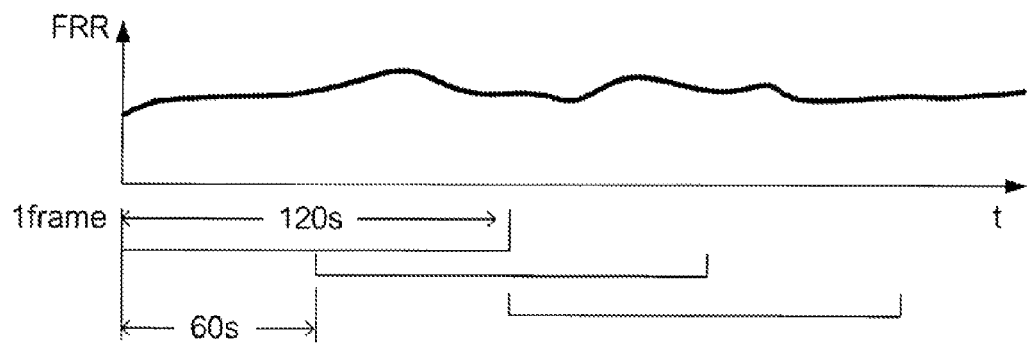
FIG. 7 is a diagram illustrating a frame when performing frequency analysis of an RR waveform signal.

FIG. 7 is a diagram illustrating a frame when performing frequency analysis of the RR waveform signal FRR. The waveform shown in FIG. 7 is an example of the waveform of the RR waveform signal FRR. As shown in FIG. 7, the period of each frame is 120 seconds in this example, and frequency analysis is performed after sampling every 60 seconds. That is, each frame is set so as to be shifted by 60 seconds, and overlaps the next frame for 60 seconds.

In addition, the above-described calculation frequency band from which band power is calculated by the power calculation unit 113 is determined in advance. In this example, the above-described calculation frequency band is assumed to be a band of 0.25 Hz to 0.5 Hz. This is determined as between two valleys (valleys of 0.25 Hz and 0.5 Hz)) of the frequency characteristics shown in FIG. 6. The reason is that power in a valley portion hardly contributes to the determination of the presence of atrial fibrillation since the power in a valley portion is suppressed. For this reason, the calculation frequency band is determined to focus on a portion that contributes to the determination of the presence of atrial fibrillation. That is, the calculation frequency band may be set to be a narrow range in such a manner that a valley portion in the frequency characteristics is removed and only a mountain portion is included. For example, the calculation frequency band may be a band of 0.3 Hz to 0.45 Hz.

In addition, in this example, the maximum frequency (upper limit) and the minimum frequency (lower limit) of the calculation frequency band are determined according to the frequency characteristics in the RR interval calculation unit 112, that is, the period of a frame used in the frequency analysis of the RR interval calculation unit 112. On the other hand, one or both of the upper and lower frequencies do not necessarily need to be determined according to the period of a frame.

As shown in FIGS. 10A, 10B, 11A, and 11B, the minimum frequency of the calculation frequency band may be set to be equal to or higher than 0.1 Hz at which a change in power becomes apparent. Preferably, the minimum frequency of the calculation frequency band may be set to be equal to or higher than 0.2 Hz. In this case, as described above, it is preferable that the minimum frequency be equal to or greater than the reciprocal of the period of the frame used in the frequency analysis of the RR interval calculation unit 112.

In addition, it is preferable that the maximum frequency of the calculation frequency band be equal to or less than ½ of the sampling frequency in frequency analysis of the RR interval calculation unit 112 in consideration of the influence of the Nyquist frequency. In this case, as described above, it is preferable that the maximum frequency be equal to or less than twice the reciprocal of the period of the frame used in the frequency analysis of the RR interval calculation unit 112.

Referring back to FIG. 4, explanation is continued. The variation coefficient calculation unit 116 calculates a variation coefficient CVRR from the RR waveform signal FRR (average pulse wave RR interval), which is stored in the RR waveform signal storage region 122, according to the following Expression (1).

$$CVRR = \sigma RR / aveRR \quad (1)$$

In addition, σRR and aveRR indicate a standard deviation and an average value of the average pulse wave RR interval in the period of one frame, respectively. That is, the variation coefficient CVRR is a parameter indicating the degree of a variation with respect to an average. The variation coefficient calculation unit 116 stores the calculated variation coefficient CVRR in the variation coefficient waveform storage region 124. Since the variation coefficient CVRR is calculated for each frame, a signal (hereinafter, referred to as a "variation coefficient signal Sc") indicating a temporal change of the variation coefficient CVRR is stored in the variation coefficient waveform storage region 124. In addition, the variation coefficient signal Sc is a set of data indicating a temporal change of the variation coefficient CVRR.

The analysis unit 114 analyzes the presence of atrial fibrillation at each time on the basis of the power waveform signal Pa stored in the power waveform signal storage region 123 and the variation coefficient signal Sc stored in the variation coefficient waveform storage region 124. Specifically, the analysis unit 114 determines whether or not these signals satisfy specific determination conditions and outputs information according to the determination result. The specific determination conditions will be described later.

When it is determined that the determination result is atrial fibrillation, the analysis unit 114 outputs information indicating the determination result to the display control unit 115. The information output from the analysis unit 114 may be information regarding the presence of atrial fibrillation, for example, information indicating the determination as atrial fibrillation. The display control unit 115 controls the display content of the display unit 15 on the basis of the information output from the analysis unit 114, and displays an image showing that determination as atrial fibrillation has been made. The user can check whether or not determination as atrial fibrillation has been made by viewing this display content. In addition, this display content may be a display showing a determination result of atrial fibrillation in real time, or may be a display showing a period determined to be atrial fibrillation.

The above is an explanation of the functional configuration of the atrial fibrillation analyzer 100. Subsequently, the analysis operation (atrial fibrillation analysis process) of the atrial fibrillation analyzer 100 will be described with reference to FIG. 9.

Atrial Fibrillation Analysis Process

Figure 9:
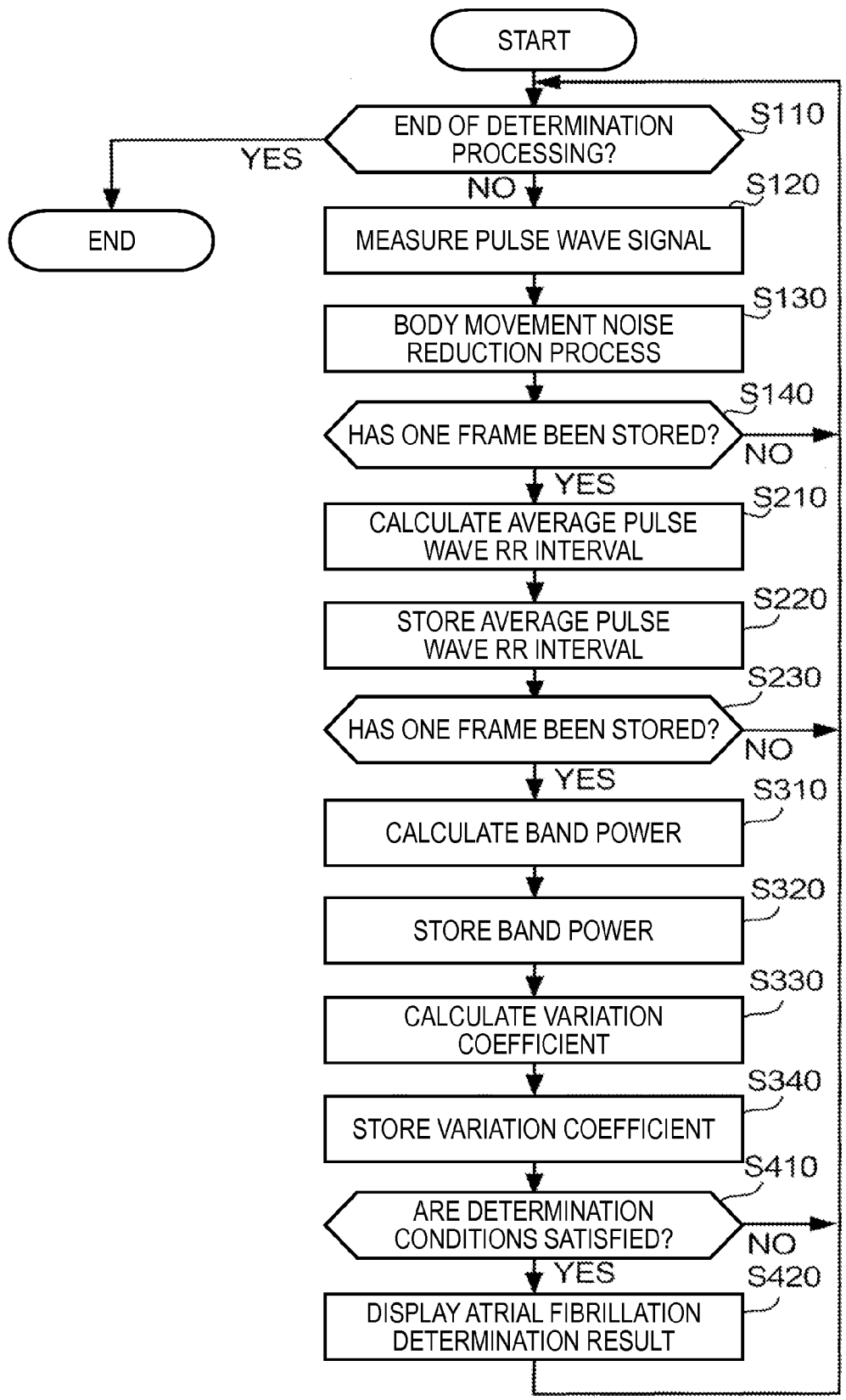
FIG. 9 is a flowchart of an atrial fibrillation analysis process.

FIG. 9 is a flowchart illustrating an atrial fibrillation analysis process in the embodiment. First, when a user operates the operation unit 14 to input an instruction to start the atrial fibrillation analysis process, the CPU 11 starts the flow shown in FIG. 9. The CPU 11 determines whether or not the user has operated the operation unit 14 to input an instruction to end the analysis process (step S110). When an instruction to end the analysis process is input (step S110; YES), the CPU11 ends the atrial fibrillation analysis process.

When an instruction to end the analysis process is not input (step S110; NO), the CPU 11 measures the detected waveform signal L by detecting a pulse wave using the pulse wave detector 20 (step S120), and performs a body movement noise reduction process using the noise reduction unit 111 (step S130). In this case, the CPU 11 stores the detected waveform signal L in the detected waveform signal storage region 121 of the RAM 12. However, the detected waveform signal L after the body movement noise reduction process may be stored.

The CPU 11 determines whether or not the waveform signal after the body movement noise reduction process is stored by one frame in the RAM 12 (step S140). When one frame is not stored (step S140; NO), the CPU 11 returns to step S110 to continue the process. On the other hand, when one frame is stored (step S140; YES), the CPU 11 calculates an average pulse wave RR interval using the RR interval calculation unit 112 (step S210).

The CPU 11 stores the average pulse wave RR interval calculated by the RR interval calculation unit 112 in the RR waveform signal storage region 122 (step S220). A temporal change of the average pulse wave RR interval stored in the storage region is the RR waveform signal FRR.

The CPU 11 determines whether or not the RR waveform signal FRR stored in the RR waveform signal storage region 122 is stored by one frame (step S230). When one frame is not stored (step S230; NO), the CPU 11 returns to step S110 to continue the process. On the other hand, when one frame is stored (step S230; YES), the CPU 11 calculates band power using the power calculation unit 113 (step S310).

The CPU 11 stores the band power calculated by the power calculation unit 113 in the power waveform signal storage region 123 (step S320). A temporal change of the band power stored in the storage region is the power waveform signal Pa.

The CPU 11 calculates a variation coefficient using the variation coefficient calculation unit 116 (step S330). The CPU 11 stores the variation coefficient calculated by the variation coefficient calculation unit 116 in the variation coefficient waveform storage region 124 (step S340).

The CPU 11 causes the analysis unit 114 to determine whether or not the power waveform signal Pa and the variation coefficient signal Sc satisfy predetermined determination conditions with reference to the power waveform signal Pa and the variation coefficient signal Sc that are stored (step S410).

Figure 12:
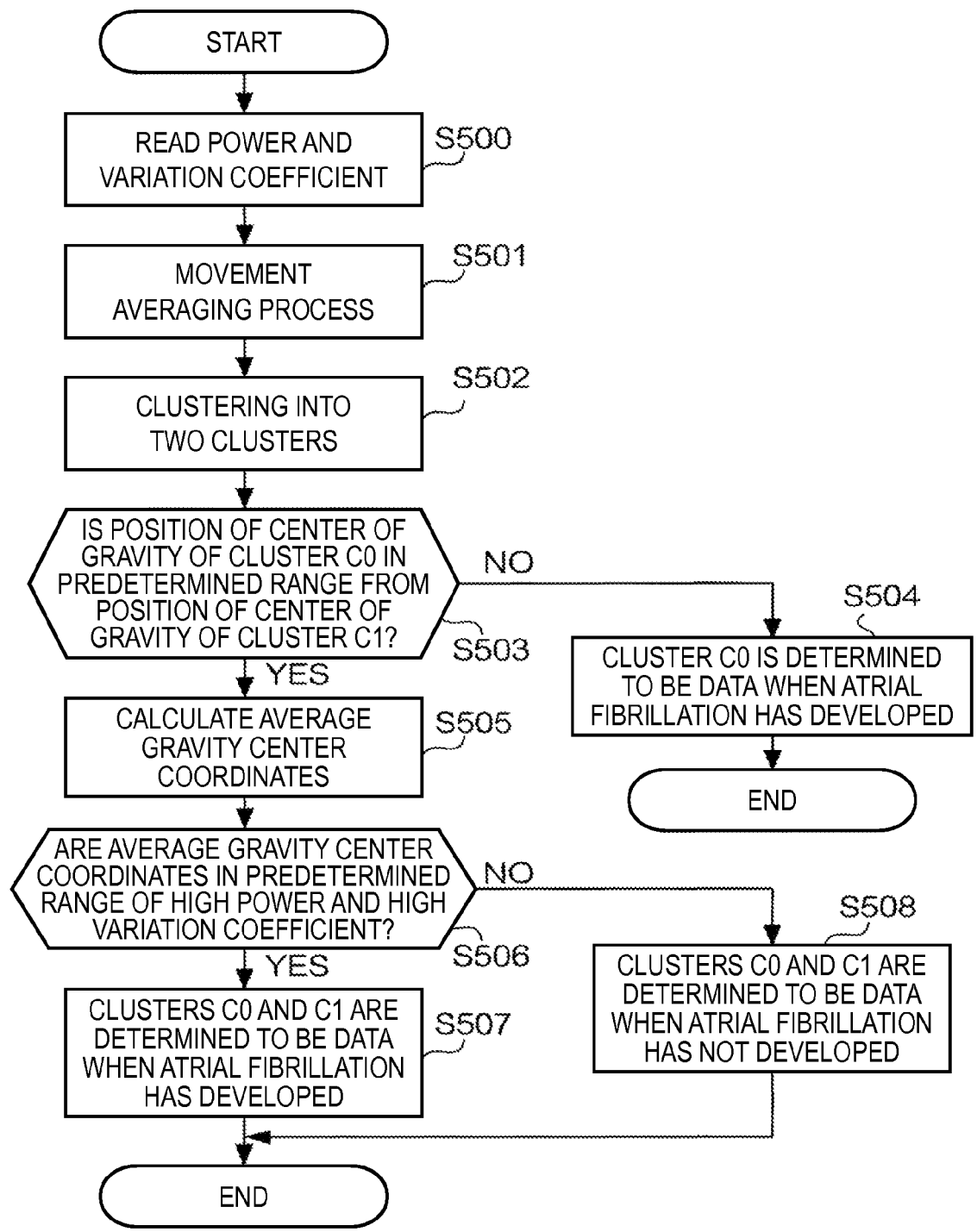
FIG. 12 is a diagram showing the details of the atrial fibrillation analysis process in step S410 of FIG. 9.

FIG. 12 is a diagram showing the details of the atrial fibrillation analysis process in step S410. In step S500, the CPU 11 reads the power waveform signal Pa and the variation coefficient signal Sc from the RAM 12.

Figure 13:
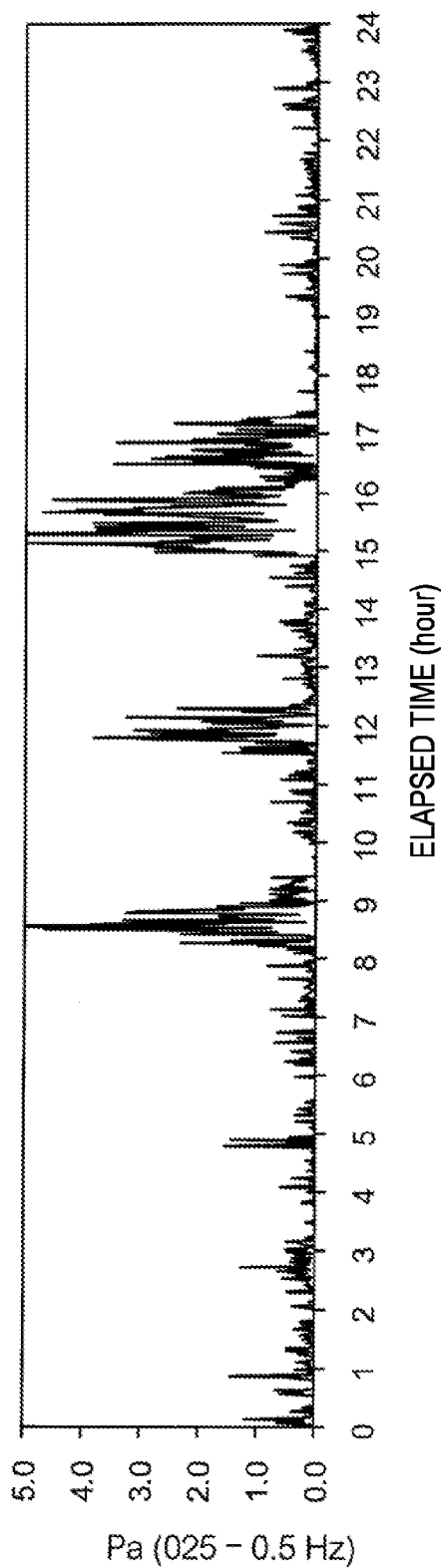
FIG. 13 is a diagram illustrating a power waveform signal and a variation coefficient signal.
Figure 13:
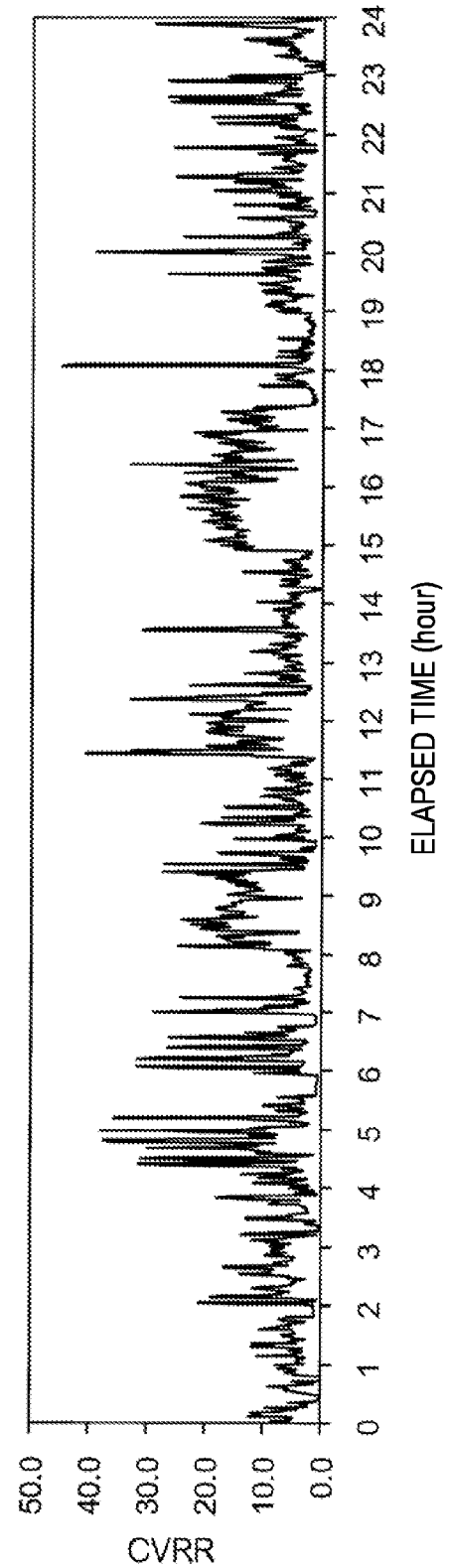

FIG. 13 is a diagram illustrating the power waveform signal Pa and the variation coefficient signal Sc. FIG. 13 shows the power waveform signal Pa [msec2] and the variation coefficient signal Sc [%] obtained from a pulse wave signal measured for 24 hours for a certain patient. In addition, this patient has developed atrial fibrillation during the measurement period.

FIG. 12 is referred to again. In step S501, the CPU 11 performs a movement averaging process on the power waveform signal Pa and the variation coefficient signal Sc. The movement averaging process is performed in order to smooth small variations (variations in a short time) for each of the power and the variation coefficient CVRR. In this example, the movement averaging process is performed using the data (that is, data obtained from the 20-minute measurement of the pulse wave) of 20 points.

Figure 14:
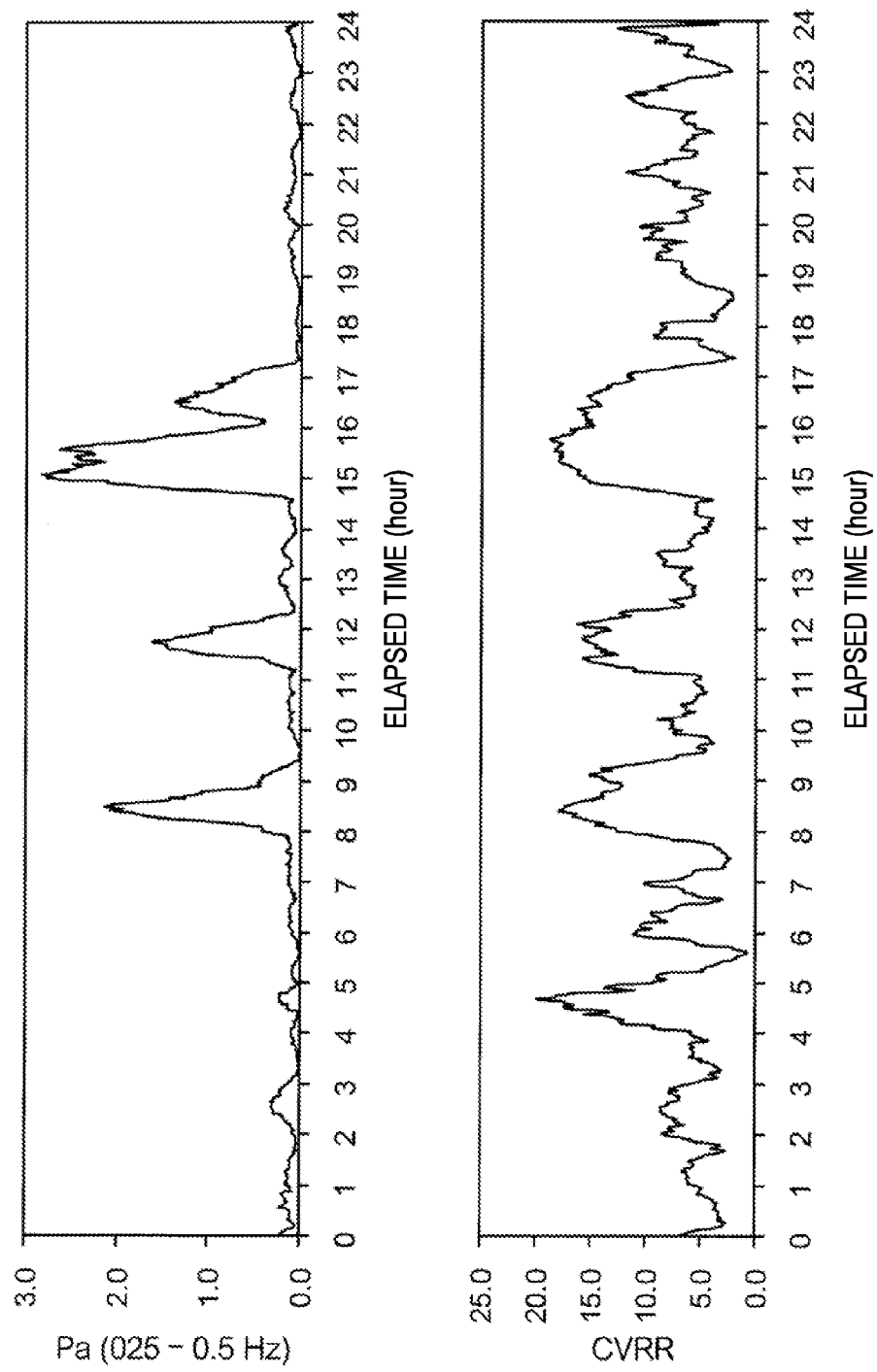
FIG. 14 is a diagram illustrating power and a variation coefficient after a movement averaging process.

FIG. 14 is a diagram illustrating the power waveform signal Pa and the variation coefficient signal Sc after the movement averaging process. Small variations are smoothed by the movement averaging process. Hereinafter, the data after the movement averaging process is treated as data showing the power and the variation coefficient at a certain time. Since the measurement is performed every 60 seconds, the data of 1440 points is obtained in the measurement of 24 hours.

FIG. 12 is referred to again. In step S502, the CPU 11 clusters the data into two clusters using a predetermined algorithm (for example, a k-means method widely known as a method of clustering).

Figure 15:
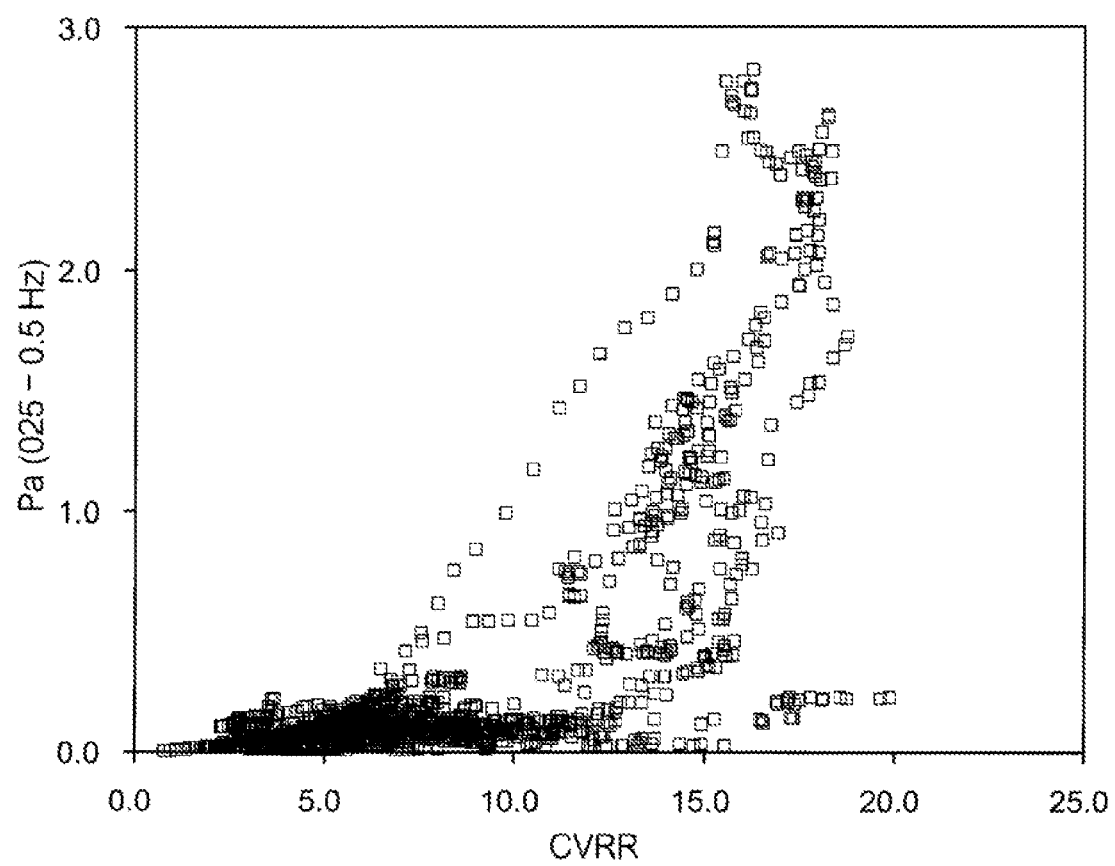
FIG. 15 is a diagram illustrating the relationship between the power and the variation coefficient.

FIG. 15 is a diagram illustrating the relationship between the power and the variation coefficient. The vertical axis indicates power [msec2], and the horizontal axis indicates the variation coefficient CVRR [%]. As previously described, the values of the power and the variation coefficient when atrial fibrillation has developed are relatively high compared with those at the normal time. Accordingly, it is thought that the plot near the upper right in FIG. 15 corresponds to data measured when atrial fibrillation has developed. In the present embodiment, data is divided into two clusters using a clustering method, and the presence of atrial fibrillation is analyzed on the basis of the positional relationship of the two clusters in variation coefficient-power space.

Figure 16:
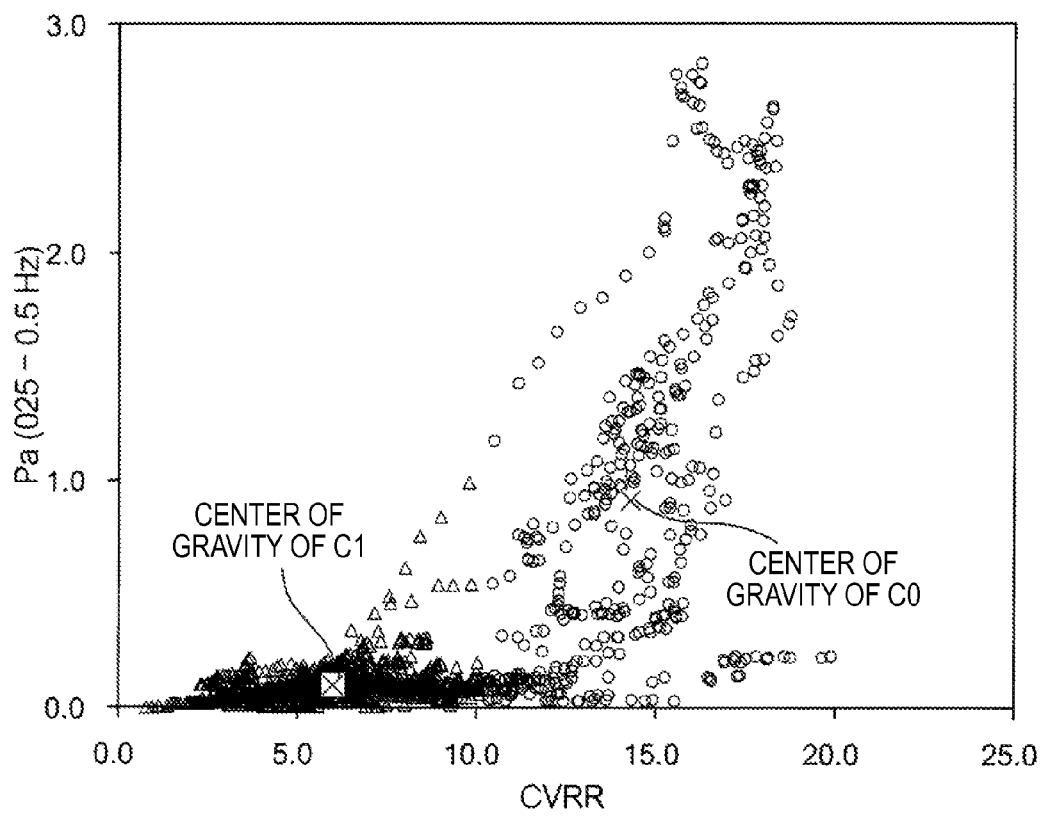
FIG. 16 is a diagram illustrating a result after clustering of data shown in FIG. 15.

FIG. 16 is a diagram illustrating a result after clustering of the data shown in FIG. 15. Thus, data is divided into two clusters using the clustering method (in this example, the k-means method). These two clusters are called a cluster C0 and cluster C1. The cluster C0 is a data group of relatively high variation coefficients and relatively high power, and the cluster C1 is a data group of relatively low variation coefficients and relatively low power. The data of the cluster C0 is expressed by a circle (○), and the cluster C1 is expressed by a triangle (Δ). In addition, according to the k-means method, the coordinates of the center of gravity of each cluster in the variation coefficient-power space are calculated. In FIG. 16, the positions of the centers of gravity of the clusters C0 and C1 are shown together.

FIG. 12 is referred to again. In step S503, the CPU 11 determines whether or not the position of the center of gravity of the cluster C0 is in a predetermined range, for example, a range of ±30% with the position of the center of gravity of the cluster C1 as a reference. When it is determined that the position of the center of gravity of the cluster C0 is outside the range of ±30% from the position of the center of gravity of the cluster C1 (S503; NO), the CPU 11 proceeds to step S504. When it is determined that the position of the center of gravity of the cluster C0 is within the range of ±30% from the position of the center of gravity of the cluster C1 (S503; YES), the CPU 11 proceeds to step S505.

In step S504, the CPU 11 determines that the cluster C0 is data when atrial fibrillation has developed.

When the position of the center of gravity of the cluster C0 is within the range of ±30% from the position of the center of gravity of the cluster C1, it is determined that the data cannot be divided into two clusters. In this case, as the possibility, a case where atrial fibrillation has not developed in the entire measurement period and a case where atrial fibrillation continues to develop in the entire measurement period can be considered. In these cases, the presence of atrial fibrillation is analyzed on the basis of the values of power and the variation coefficient. This process is performed from step S505.

In step S505, the CPU 11 calculates the coordinates (hereinafter, referred to as "average gravity center coordinates") of the average position (hereinafter, referred to as "average center of gravity") of the center of gravity of the cluster C0 and the center of gravity of the cluster C1. The average center of gravity is a simple average of the center of gravity of the cluster C0 and the center of gravity of the cluster C1 (that is, a midpoint of the center of gravity of the cluster C0 and the center of gravity of the cluster C0, for example. Alternatively, the average center of gravity may also be the weighted center (that is, the center of gravity of all measurement points) according to the number of data points of the center of gravity of the cluster C0 and the center of gravity of the cluster C1.

In step S506, the CPU 11 determines whether or not the average gravity center coordinates are in a predetermined range (for example, a variation coefficient of 10.0 or more and power of 0.5 or more). When it is determined that the average gravity center coordinates are in a predetermined range (S506; YES), the CPU 11 determines that atrial fibrillation has developed in the entire measurement period (step S507). When it is determined that the average gravity center coordinates are not in a predetermined range (S506; NO), the CPU 11 determines that atrial fibrillation has not developed in the entire measurement period (step S508).

FIG. 9 is referred to again. When it is determined that atrial fibrillation has not developed (step S410; NO), the CPU 11 returns to step S110 to continue the process. On the other hand, when it is determined that atrial fibrillation has developed (step S410; YES), the CPU 11 causes the display control unit 115 to display the determination result, which indicates that atrial fibrillation has developed, on the display unit 15 (step S420), and returns to step S110 to continue the process.

In addition, the CPU 11 may repeat the process of steps S110 to S140 regardless of the determination result in step S140. In this case, the CPU 11 may execute the process from step S210 in parallel with the process of steps S110 to S140 whenever the determination result in step S140 is YES. In this case, when the determination result in step S230 is NO or when the determination result in step S410 is NO, it is preferable to terminate the process from step S210 executed in parallel.

The above is an explanation of the atrial fibrillation analysis process.

Figure 8:
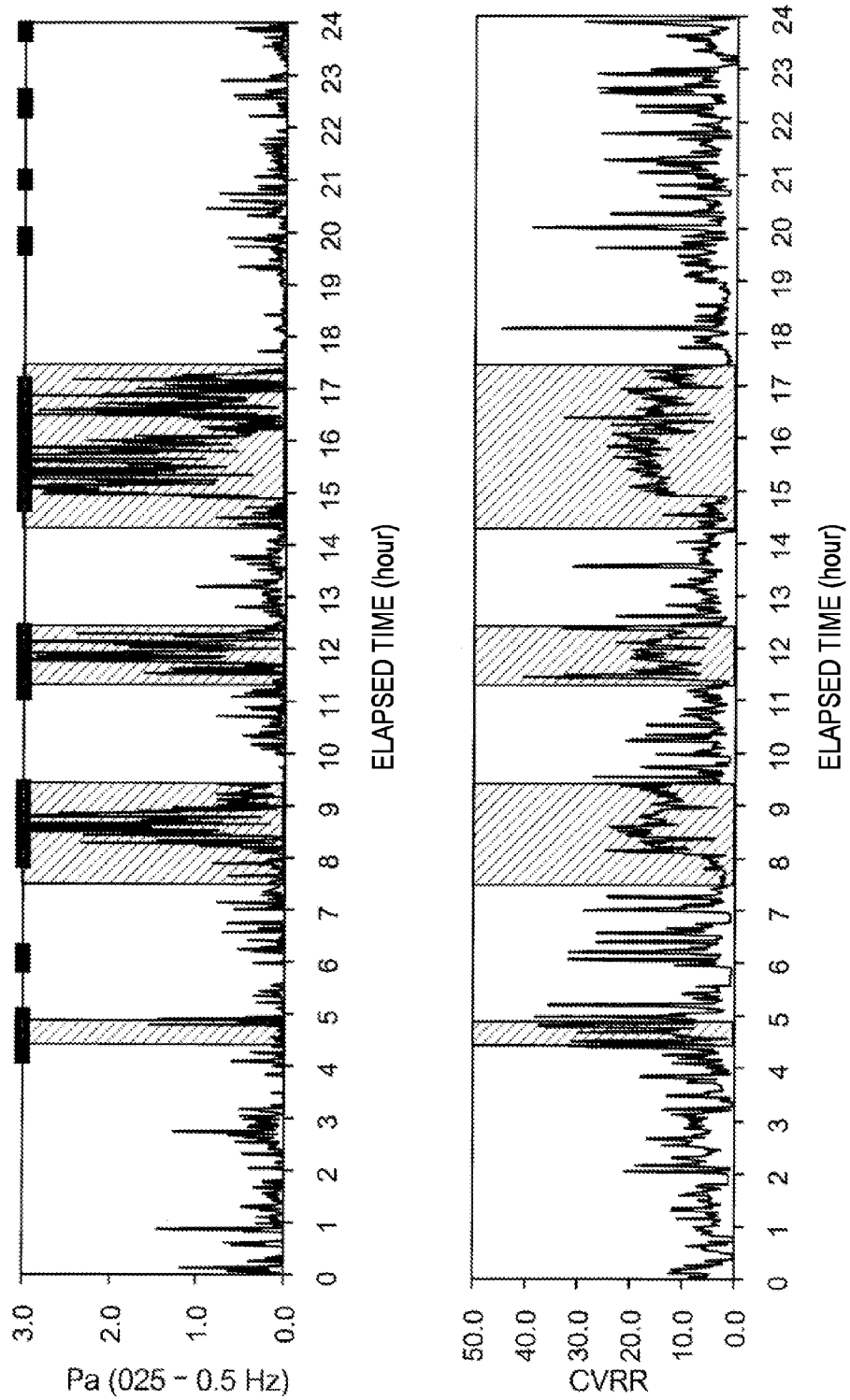
FIG. 8 is a diagram showing a determination result in the present embodiment.

FIG. 8 is a diagram showing an analysis result in the present embodiment. For comparison, a period analyzed that atrial fibrillation has developed by electrocardiogram analysis using a Holter monitor is shown together. In FIG. 8, a portion indicated by the thick line is a period analyzed that atrial fibrillation has developed in the present embodiment, and a hatched portion is a period analyzed that atrial fibrillation has developed by electrocardiogram analysis using the Holter monitor. For the period analyzed that atrial fibrillation has developed by the Holter monitor, an analysis showing that atrial fibrillation has developed is also obtained in the present embodiment with almost no exception. In the present embodiment, some noise is detected as atrial fibrillation. However, for example, when analysis as atrial fibrillation has been made in a period shorter than a predetermined threshold value, the analysis result may be rejected (that is, when analysis as atrial fibrillation has been continuously made in a period longer than the threshold value, the analysis result indicating that atrial fibrillation has developed is adopted).

Thus, in the pulse wave measuring device 1 according to the embodiment of the invention, it is possible to analyze atrial fibrillation while reducing the influence of body movement noise by measuring the average pulse wave RR interval instead of the pulse wave RR interval of each beat.

Storage Process

Next, a process of storing various kinds of data by the atrial fibrillation analyzer 100 will be described.

As shown in FIG. 4, the measurement unit 16 outputs information indicating the amount of activity of the user to the atrial fibrillation analyzer 100. This output may be performed periodically or may be performed in response to the request from the atrial fibrillation analyzer 100. Alternatively, this output may be performed when the amount of activity measured by the measurement unit 16 satisfies predetermined conditions, for example, when the amount of activity measured by the measurement unit 16 exceeds a predetermined threshold value. The amount of activity output from the measurement unit 16 is stored in the activity amount storage region 125 together with the time when the amount of activity has been measured by referring to the measurement time of the timer circuit 17.

Range information indicating a range where the amount of activity of the user can be changed is stored in the range storage region 128. For the amount of activity of the user, there are individual differences due to various factors, such as age, constitution, and lifestyle of the user. The range information stored in the range storage region 128 is information indicating the upper and lower limits of the amount of activity of the user wearing the pulse wave measuring device 1. The lower limit of the amount of activity is, for example, the amount of activity when the user takes a rest. The upper limit of the amount of activity is, for example, the amount of activity when the user feels unbearable load since the user has moved the body.

When the user operates the operation button 140 or the like of the operation unit 14, the CPU 11 stores the range information of the user in the range storage region 128 in response to this operation. In addition, range information of a plurality of users may be stored in advance in the range storage region 128 so as to match the identification information of each user. In this case, the CPU 11 may receive the operation of the user through the operation unit 14, perform authentication processing to identify the user, and extract the range information corresponding to the user from the range storage region 128.

The conversion unit 117 converts the amount of activity stored in the activity amount storage region 125 into the amount of load indicating the load for the user on the basis of the range information stored in the range storage region 128. For example, the amount of load may be expressed by numeric values when the range of the amount of activity indicated by the range information is divided into a plurality of stages, or may be expressed by the calories consumed by the activity. The consumed calories may be estimated from the range of the amount of activity indicated by the range information and the value of basal metabolism set for each user, for example.

In the threshold value storage region 129, a threshold value that is compared with the amount of activity or the amount of load of the user is stored. Here, the threshold value storage region 129 stores a threshold value compared with the amount of load of the user. The notification unit 119 compares the amount of load of the user obtained by the conversion of the conversion unit 117 with the threshold value of the user stored in the threshold value storage region 129. When the amount of load of the user exceeds the threshold value, the notification unit 119 notifies the user of the result so that the user operates the operation unit 14. Specifically, when it is determined that the amount of load of the user exceeds the threshold value, the notification unit 119 outputs a predetermined signal to the display control unit 115. When this signal is received, the display control unit 115 displays, for example, a screen prompting the user to press the action button 141 on the display unit 15.

When the action button 141 provided in the operation unit 14 is pressed by the user, a unique signal assigned to the action button 141 is output to the atrial fibrillation analyzer 100. When this signal is received, the atrial fibrillation analyzer 100 stores the signal in the action data storage region 126 as "action data". The action data is stored in the action data storage region 126 each time the action button 141 is pressed by referring to the time measured by the timer circuit 17 in the atrial fibrillation analyzer 100.

When the subjective symptom button 142 provided in the operation unit 14 is pressed by the user, a unique signal assigned to the subjective symptom button 142 is output to the atrial fibrillation analyzer 100. When this signal is received, the atrial fibrillation analyzer 100 stores the signal in the subjective symptom data storage region 127 as "subjective symptom data". The subjective symptom data is stored in the subjective symptom data storage region 127 each time the subjective symptom button 142 is pressed by referring to the time measured by the timer circuit 17 in the atrial fibrillation analyzer 100.

The evaluation unit 118 acquires the amount of load converted by the conversion unit 117 each time the amount of activity corresponding to the load is measured by the measurement unit 16. In addition, the evaluation unit 118 acquires information indicating the presence of atrial fibrillation analyzed by the analysis unit 114 each time the atrial fibrillation has developed or each time the atrial fibrillation has disappeared. In addition, the evaluation unit 118 evaluates the amount of activity, which has been measured by the measurement unit 16 during the period (onset period) analyzed that there is atrial fibrillation (atrial fibrillation has developed) by the analysis unit 114, or the amount of load converted from the amount of activity. This evaluation is based on the comparison between the average value of the amount of load for the entire period and the average value of the amount of load converted from the amount of activity measured during the period analyzed that there is atrial fibrillation. This evaluation is performed by calculating by what percentage the amount of load during the period analyzed that there is atrial fibrillation has increased compared with the entire amount of load and presenting the result. In addition, this evaluation may be performed by expressing a graph of the amount of load in the period analyzed that there is atrial fibrillation in different color from the color of a graph of the amount of load in the other period. That is, by the evaluation of the evaluation unit 118, information may be processed so that the measured amount of activity or the amount of load corresponding to the amount of activity is distinguished according to the presence of atrial fibrillation.

In addition, the evaluation unit 118 may read the action data from the action data storage region 126, or may read the subjective symptom data from the subjective symptom data storage region 127. In addition, the evaluation unit 118 may arrange the amount of activity measured by the measurement unit 16 or the amount of load corresponding to the amount of activity in time series and express the amount of activity or the load in such a manner that it can be contrasted with the time when the action button 141 is pressed, the time when the subjective symptom button 142 is pressed, and the like.

Thus, the pulse wave measuring device 1 according to the embodiment of the invention can display the relationship between the onset of atrial fibrillation and the amount of activity. Therefore, for example, the doctor B who views this display can diagnose the symptom of the patient A, to whom the pulse wave measuring device 1 has been lent, by associating the symptom with the amount of activity.

MODIFICATION EXAMPLES

While the embodiment of the invention has been described, the invention can be implemented in various ways as follows.

Modification Example 1

In the embodiment described above, the detected waveform signal L is a signal indicating the pulse wave detection result of the pulse wave detector 20. However, the detected waveform signal L may also be a waveform signal obtained as an electrocardiogram detection result. That is, the detected waveform signal L may be a waveform signal from which a parameter equivalent to the RR interval can be acquired.

Modification Example 2

In the embodiment described above, the noise reduction unit 111 is provided as a functional configuration of the atrial fibrillation analyzer 100. However, the noise reduction unit 111 does not necessarily need to be provided. In this case, the RR interval calculation unit 112 may acquire the detected waveform signal L for frequency analysis from the detected waveform signal storage region 121.

Modification Example 3

In the embodiment described above, the atrial fibrillation analyzer 100 may be realized in the pulse wave measuring device 1. However, the atrial fibrillation analyzer 100 may also be realized in an information processing apparatus, such as a personal computer. In this case, the information processing apparatus may acquire the detected waveform signal L measured in advance from an external device and store the detected waveform signal L in the detected waveform signal storage region 121. Then, the information processing apparatus may analyze the presence of atrial fibrillation by analyzing the detected waveform signal L by atrial fibrillation analysis process.

Modification Example 4

In the embodiment described above, the device body 10 and the pulse wave detector 20 are connected to each other using the cable 30. However, the device body 10 and the pulse wave detector 20 may be wirelessly connected to each other. In this case, the device body 10 and the pulse wave detector 20 may exchange various signals, such as a control signal required for the control of the pulse wave detector 20 and the detected waveform signal L generated by the pulse wave detector 20, therebetween by wireless communication. In addition, each of the device body 10 and the pulse wave detector 20 may be made to have a configuration of a battery that can supply electric power thereto.

Modification Example 5

In the embodiment described above, the analysis result of atrial fibrillation is displayed on the display unit 15 and is notified to the user. However, the analysis result of atrial fibrillation may also be notified by sound, vibration, or the like. For example, when notifying the user of the atrial fibrillation analysis result using sound, it is preferable to provide a speaker and a sound control unit that controls the content of sound output from the speaker on the basis of the information from the analysis unit 114. For example, when notifying the user of the atrial fibrillation analysis result using vibration, it is preferable to provide a vibration actuator and a vibration control unit that controls the vibration content of the vibration actuator on the basis of the information from the analysis unit 114. Thus, the display control unit 115 and the display unit 15 in the embodiment can also be conceptualized as a notification unit that notifies the user according to the analysis result of atrial fibrillation.

Modification Example 6

Various parameters described in the embodiment, for example, the threshold value (±30%) of cluster separation, the predetermined range (variation coefficient of 10.0 or more and power of 0.5 or more) with respect to the average gravity center coordinates, the number of data points (20 points) of the movement averaging process, and the frame period (120 seconds) are examples, and the values of these parameters are not limited thereto. In addition, the algorithm of clustering is not limited to the k-means method. A data group constellation may be separated into two clusters by algorithms other than the k-means method. In addition, the specific method of analyzing the presence of atrial fibrillation is not limited to that described in FIG. 12. For example, the presence of atrial fibrillation may be analyzed by methods other than the method described in FIG. 12, such as comparing at least one of the power and the variation coefficient with a threshold value.

Modification Example 7

A control program in the embodiment described above can be provided in a state of being stored on a computer-readable recording medium, such as a magnetic recording medium (a magnetic tape, a magnetic disk, or the like), an optical recording medium (optical disc or the like), a magneto-optical recording medium, and a semiconductor memory. In addition, the pulse wave measuring device 1 may download each program through a network.

Modification Example 8

Figure 17:
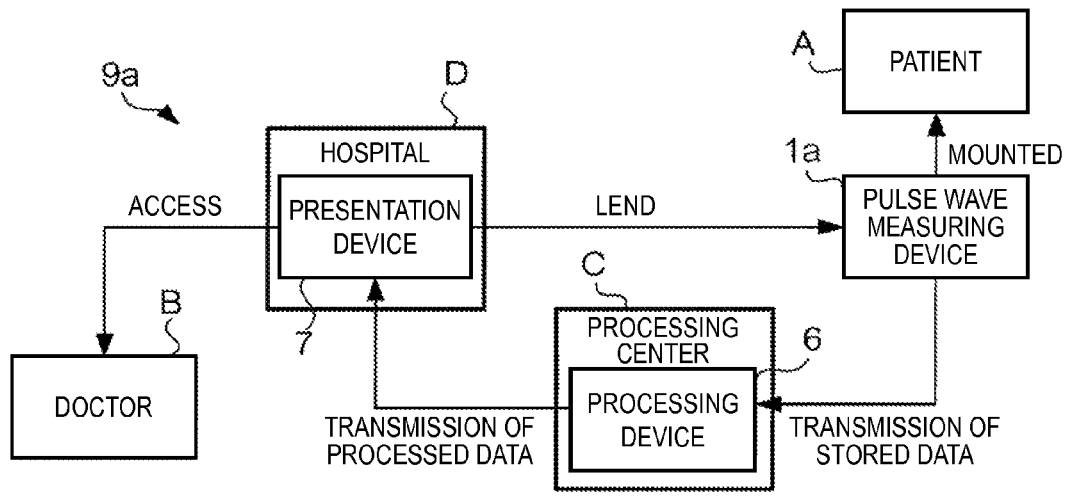
FIG. 17 is a diagram showing the configuration of an atrial fibrillation analysis system in a modification example.

In the embodiment described above, the processing function of the processing center C of the atrial fibrillation analysis system 9 is included in the pulse wave measuring device 1. However, the atrial fibrillation analysis system may use the processing center C separately from the pulse wave measuring device 1. FIG. 17 is a diagram showing the configuration of an atrial fibrillation analysis system 9a in a modification example. The atrial fibrillation analysis system 9a includes a pulse wave measuring device 1a, a processing device 6, and a presentation device 7. Both the processing device 6 and the presentation device 7 are formed by a personal computer and the like.

A hospital D owns the pulse wave measuring device 1a, and lends the pulse wave measuring device 1a to the patient A for a determined period, such as 10 days. The patient A to whom the pulse wave measuring device 1a has been lent wears the pulse wave measuring device 1a on his or her wrist as shown in FIGS. 2A and 2B so that the pulse wave measuring device 1a performs pulse wave measurement and atrial fibrillation analysis. After the period described above has passed, various kinds of data stored in the pulse wave measuring device 1a are transmitted to the processing device 6 provided in the processing center C. Data transmission may be performed through a dedicated line or a public line, or may be performed by cable or wirelessly. In this case, the pulse wave measuring device 1a includes a communication unit 101 indicated by the dotted line in FIG. 3, and data transmission is performed through the communication unit 101. The communication unit 101 is an interface for information communication between the pulse wave measuring device 1a and the processing device 6. Examples of the communication unit 101 include various kinds of modems, wireless communication circuits, and serial interfaces. In addition, a member of the processing center C may connect the pulse wave measuring device 1a delivered from the patient A to the processing device 6, and read the above-described data into the processing device 6.

The processing device 6 has the same function as the evaluation unit 118 of the pulse wave measuring device 1 in the embodiment described above, and processes the data acquired from the pulse wave measuring device 1a. In addition, in this case, the pulse wave measuring device 1a may not include the evaluation unit 118 of the pulse wave measuring device 1. The pulse wave measuring device 1a transmits to the processing device 6 the time series data of the amount of load converted by the conversion unit 117 and the time series data of the information indicating the presence of atrial fibrillation analyzed by the analysis unit 114. Among the received amounts of load, the processing device 6 evaluates the amount of load converted from the amount of activity measured by the measurement unit 16 during the period analyzed that there is atrial fibrillation by the analysis unit 114. Then, the processing device 6 processes the data on the basis of the evaluation result of the amount of load, so that the amount of load (or the amount of activity corresponding to the amount of load) at each time is distinguished according to the presence of atrial fibrillation.

The data processed by the processing device 6 is transmitted to the presentation device 7. The presentation device 7 includes a display screen, such as a liquid crystal, and presents the processed data to the doctor B by displaying an image corresponding to the data transmitted from the processing device 6 on the display screen, for example.

Thus, since the atrial fibrillation analysis system 9a can present the relationship between the onset of atrial fibrillation and the amount of activity, the doctor B who uses the atrial fibrillation analysis system 9a can diagnose the atrial fibrillation of the patient A by associating the onset of atrial fibrillation with the amount of activity. Specifically, the doctor B can diagnose whether the patient A is of a type in which the symptom (atrial fibrillation) is likely to occur when the amount of activity is low, such as at night, or a type in which the symptom (atrial fibrillation) is likely to occur when the amount of activity is high due to vigorous exercise or the like by using the atrial fibrillation analysis system 9a.

Figure 18:
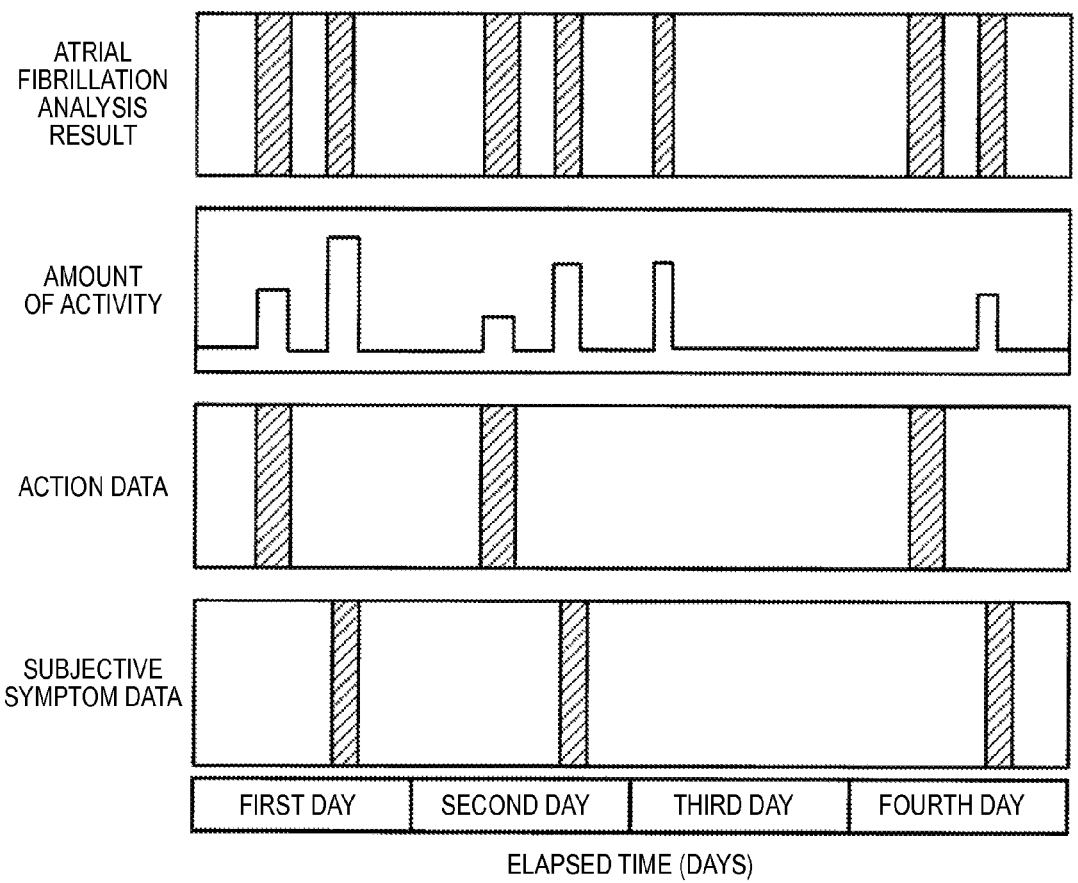
FIG. 18 is a diagram showing an example of a graph that expresses data in such a manner that the data can be contrasted with each other.

In addition, the processing device 6 may acquire action data from the pulse wave measuring device 1a, or may acquire subjective symptom data from the pulse wave measuring device 1a. In addition, the processing device 6 may arrange the amount of activity measured by the measurement unit 16 or the amount of load corresponding to the amount of activity in time series and express the amount of activity or the load in such a manner that it can be contrasted with the time when the action button 141 is pressed, the time when the subjective symptom button 142 is pressed, and the like. FIG. 18 is a diagram showing an example of a graph that expresses these data items in such a manner that they can be contrasted with each other. In the graph shown in FIG. 18, the horizontal axis indicates elapsed time, and an atrial fibrillation analysis result, the amount of activity, action data, and subjective symptom data are arranged in time series in such a manner that they can be contrasted with each other. The doctor B to whom the data processed in this manner is presented diagnoses the type of the symptom of the patient A, for example, by checking the degree of matching between a period for which the amount of activity has increased and a period analyzed that atrial fibrillation has developed. In addition, the doctor B can diagnose if the patient A should be careful of the onset of a disease according to what kind of action the patient A performs and also can diagnose the sensitivity of awareness for the symptom of the patient A by comparing the time when the action button 141 is pressed or the time when the subjective symptom button 142 is pressed with the time analyzed that atrial fibrillation has developed.

Modification Example 9

In the embodiment or the modification examples described above, the evaluation unit 118 of the pulse wave measuring device 1 or the processing device 6 acquires the data of the amount of load converted by the conversion unit 117 and evaluates the amount of load. However, it is also possible to acquire the data of the amount of activity before being converted and evaluate the amount of activity. In this case, the pulse wave measuring device 1 may not include the conversion unit 117.

In addition, in the embodiment or the modification examples described above, the operation unit 14 of the pulse wave measuring device 1 includes the action button 141 to output a signal for storing "action data" to the atrial fibrillation analyzer 100 when operated. However, the operation unit 14 of the pulse wave measuring device 1 may not include the action button 141. In this case, the user may input action data to the pulse wave measuring device 1 by operating an input device provided outside, and the pulse wave measuring device 1 may receive the action data from the input device, which has been operated by the user, through the communication unit 101 described above. The communication unit 101 functions as a receiving unit that receives an input of action data from an input device. In addition, also in this case, the notification unit 119 compares the amount of load of the user obtained by the conversion of the conversion unit 117 with the threshold value of the user stored in the threshold value storage region 129. When the amount of load of the user exceeds the threshold value, the notification unit 119 notifies the user of the result so that the user operates an input device.

What is claimed is:

1. An atrial fibrillation analysis system, comprising:
an acquisition unit that acquires a detected waveform signal indicating a temporal change of a detection result of a pulse wave or an electrocardiogram;
a waveform storage unit that stores the acquired detected waveform signal;
an RR interval calculation unit that calculates, on the basis of a frequency spectrum of each unit time obtained by frequency analysis of the acquired detected waveform signal, a parameter corresponding to an average RR interval every unit time;
a power calculation unit that calculates power of a frequency band determined in advance in a frequency spectrum of an RR waveform signal indicating a temporal change of the average RR interval calculated by the RR interval calculation unit;
a variation coefficient calculation unit that calculates a variation coefficient of the average RR interval in the RR waveform signal;
an analysis unit that determines presence of atrial fibrillation at each time on the basis of a set of the power and the variation coefficient;
a measurement unit that measures an amount of activity of a user by detecting body movement of the user;
a first storage unit that stores the amount of activity measured by the measurement unit and a time when the amount of activity is measured so as to match each other;
an evaluation unit that evaluates the amount of activity measured by the measurement unit during onset of the atrial fibrillation to distinguish between the amount of activity in presence of the atrial fibrillation and the amount of activity in absence of the atrial fibrillation, wherein the onset of the atrial fibrillation is determined by the analysis unit;
a processing device that acquires the amount of activity measured by the measurement unit and processes data indicating the amount of activity on the basis of an analysis result of the analysis unit; and
a presentation device that presents the data processed by the processing device.

2. The atrial fibrillation analysis system according to claim 1, further comprising:
a second storage unit that stores action data acquired through an operation unit that is operated by the user, wherein the action data indicates an action of the user, at each time of the action.

3. The atrial fibrillation analysis system according to claim 2, further comprising:
a notification unit that, when the amount of activity measured by the measurement unit exceeds a predetermined threshold value, notifies the user that the amount of activity has exceeded the threshold value so that the user operates the operation unit,
wherein the second storage unit stores the action data when the operation unit is operated by the user.

4. The atrial fibrillation analysis system according to claim 2, further comprising:
a receiving unit that receives an input of the action data from an input device associated with the operation unit; and
a notification unit that, when the amount of activity measured by the measurement unit exceeds a predetermined threshold value, notifies the user that the amount of activity has exceeded the threshold value so that the user inputs the action data through the input device,
wherein the second storage unit stores the action data when the input of the action data is received by the receiving unit.

5. The atrial fibrillation analysis system according to claim 1, further comprising:
a range storage unit that stores range information indicating a range where the amount of activity of the user is changeable; and
a conversion unit that converts the amount of activity measured by the measurement unit into an amount of load, which indicates a load for the user, on the basis of the range information stored in the range storage unit.

6. The atrial fibrillation analysis system according to claim 1, further comprising:
a third storage unit that stores subjective symptom data acquired through an operation unit that is operated by the user, wherein the subjective symptom data indicates the atrial fibrillation that the user is aware of, each time the user is aware of the atrial fibrillation.

7. An atrial fibrillation analysis method, comprising:
acquiring, by an atrial fibrillation analysis system, a detected waveform signal indicating a temporal change of a detection result of a pulse wave or an electrocardiogram;
storing, by the atrial fibrillation analysis system, the acquired detected waveform signal;
calculating, by the atrial fibrillation analysis system on the basis of a frequency spectrum of each unit time obtained by frequency analysis of the acquired detected waveform signal, a parameter corresponding to an average RR interval every unit time;

calculating, by the atrial fibrillation analysis system, power of a frequency band determined in advance in a frequency spectrum of an RR waveform signal indicating a temporal change of the calculated average RR interval;

calculating, by the atrial fibrillation analysis system, a variation coefficient of the average RR interval in the RR waveform signal;

analyzing, by the atrial fibrillation analysis system, presence of atrial fibrillation at each time on the basis of a set of the power and the variation coefficient;

measuring, by the atrial fibrillation analysis system, an amount of activity of a user by detecting body movement of the user;

storing, by the atrial fibrillation analysis system, the measured amount of activity and a time when the amount of activity is measured so as to match each other;

evaluating, by the atrial fibrillation analysis system, the measured amount of activity during onset of the atrial fibrillation to distinguish between the amount of activity in presence of the atrial fibrillation and the amount of activity in absence of the atrial fibrillation, wherein the onset of the atrial fibrillation is determined by the atrial fibrillation analysis system;

acquiring, by the atrial fibrillation analysis system, the measured amount of activity and processing data indicating the amount of activity on the basis of an analysis result and presenting, by the atrial fibrillation analysis system, the processed data.

8. A non-transitory computer readable storage unit storing a program that, when executed by a computer, causes the computer to perform the steps of:

acquiring a detected waveform signal indicating a temporal change of a detection result of a pulse wave or an electrocardiogram;

storing the acquired detected waveform signal;

calculating, on the basis of a frequency spectrum of each unit time obtained by frequency analysis of the acquired detected waveform signal, a parameter corresponding to an average RR interval every unit time;

calculating power of a frequency band determined in advance in a frequency spectrum of an RR waveform signal indicating a temporal change of the calculated average RR interval;

calculating a variation coefficient of the average RR interval in the RR waveform signal;

analyzing presence of atrial fibrillation at each time on the basis of a set of the power and the variation coefficient;

measuring an amount of activity of a user by detecting body movement of the user;

storing the measured amount of activity and a time when the amount of activity is measured so as to match each other;

evaluating the measured amount of activity during onset of the atrial fibrillation to distinguish between the amount of activity in presence of the atrial fibrillation and the amount of activity in absence of the atrial fibrillation, wherein the onset of the atrial fibrillation is previously determined;

acquiring the measured amount of activity and processing data indicating the amount of activity on the basis of an analysis result; and presenting the processed data.

* * * * *